(12) United States Patent
Cech et al.

(10) Patent No.: US 12,228,467 B2
(45) Date of Patent: Feb. 18, 2025

(54) FORCE SENSING SEAT BELT SENSOR ASSEMBLY

(71) Applicant: JOYSON SAFETY SYSTEMS ACQUISITION LLC, Auburn Hills, MI (US)

(72) Inventors: Len Cech, Auburn Hills, MI (US); Lukas Scholz, Auburn Hills, MI (US); Darren Goudeau, Auburn Hills, MI (US); Joshua Ramaglia, Broken Arrow, OK (US)

(73) Assignee: JOYSON SAFETY SYSTEMS ACQUISITION LLC, Auburn Hills, MI (US)

( * ) Notice: Subject to any disclaimer, the term of this patent is extended or adjusted under 35 U.S.C. 154(b) by 384 days.

(21) Appl. No.: 17/490,647

(22) Filed: Sep. 30, 2021

(65) Prior Publication Data

US 2022/0128422 A1     Apr. 28, 2022

Related U.S. Application Data

(60) Provisional application No. 63/085,645, filed on Sep. 30, 2020.

(51) Int. Cl.
*G01L 5/10*       (2020.01)
*A61B 5/00*       (2006.01)
(Continued)

(52) U.S. Cl.
CPC .............. *G01L 5/10* (2013.01); *A61B 5/746* (2013.01); *B60Q 9/00* (2013.01); *B60R 22/46* (2013.01);
(Continued)

(58) Field of Classification Search
CPC ..... G01L 5/10; G01L 1/146; B60R 21/01544; B60R 2022/485; B60R 22/46;
(Continued)

(56) References Cited

U.S. PATENT DOCUMENTS 5,724,024 A      3/1998  Sonderegger et al.
5,835,008 A  *  11/1998  Colemere, Jr. ........ B60Q 1/441
                                                                  340/576
(Continued)

FOREIGN PATENT DOCUMENTS

DE     102014211501 A1    9/2015
DE     102014222528 A1    5/2016
(Continued)

OTHER PUBLICATIONS

WO-2017017278-A1 machine translation (Year: 2017).*
(Continued)

*Primary Examiner* — Angelina M Shudy
(74) *Attorney, Agent, or Firm* — Meunier Carlin & Curfman LLC

(57) ABSTRACT

A seat belt sensor assembly comprises a force sensor coupled to a seat belt webbing. The seat belt sensor assembly utilizes force readings from the force sensor indicating a force level above or below a predetermined threshold to determine if an action needs to be taken to control a vehicle system. Such vehicle systems could include, but are not limited to, an autonomous driving control system, an occupant health system, and a motorized seat belt retractor system. Controlling the vehicle systems could include, but is not limited to, sending audio, visual, and/or haptic warnings to vehicle occupants, including, in one embodiment, that the occupant's respiration rate is indicative of a dangerous health condition. The seat belt sensor assembly may be used in combination with a camera-based occupant monitoring (Continued)

system. In one embodiment, the occupant monitoring system can be used to selectively activate/deactivate discrete activation zones of the force sensor.

20 Claims, 24 Drawing Sheets

(51) Int. Cl.
| | |
|---|---|
| *B60Q 9/00* | (2006.01) |
| *B60R 22/46* | (2006.01) |
| *B60R 22/48* | (2006.01) |
| *B60W 60/00* | (2020.01) |
| *G01L 1/14* | (2006.01) |
| *G06V 20/59* | (2022.01) |
| *B60R 22/12* | (2006.01) |

(52) U.S. Cl.
CPC ......... *B60R 22/48* (2013.01); *B60W 60/0016* (2020.02); *G01L 1/146* (2013.01); *G06V 20/593* (2022.01); *B60R 22/12* (2013.01); *B60R 2022/4666* (2013.01); *B60R 2022/4841* (2013.01); *B60W 2420/403* (2013.01); *B60W 2540/221* (2020.02)

(58) Field of Classification Search
CPC . B60R 22/48; B60R 22/12; B60R 2022/4666; B60R 2022/4841; A61B 5/746; B60Q 9/00; B60W 60/0016; B60W 2420/42; B60W 2540/221; B60W 2420/403; G06V 20/593; G05D 1/00; B60N 2/00
See application file for complete search history.

(56) References Cited

U.S. PATENT DOCUMENTS

| | | | | |
|---|---|---|---|---|
| 5,964,478 | A * | 10/1999 | Stanley | B60R 21/01532 280/735 |
| 6,520,535 | B1 * | 2/2003 | Stanley | B60R 21/01534 180/271 |
| 6,575,902 | B1 * | 6/2003 | Burton | B60W 40/08 600/595 |
| 6,581,960 | B1 * | 6/2003 | Schondorf | B60R 21/01546 280/801.1 |
| 6,784,379 | B2 * | 8/2004 | Breed | B60R 21/01526 177/144 |
| 8,049,520 | B2 * | 11/2011 | Schleeh | B60R 21/01532 177/144 |
| 8,872,640 | B2 * | 10/2014 | Horseman | A61B 5/1114 340/576 |
| 9,234,924 | B2 * | 1/2016 | Dawson | A61B 5/274 |
| 9,848,814 | B2 * | 12/2017 | Benson | B60N 2/976 |
| 9,878,689 | B1 * | 1/2018 | Jimenez | B60R 21/01544 |
| 10,124,762 | B2 * | 11/2018 | Hennes | B60R 22/48 |
| 10,191,550 | B1 * | 1/2019 | Nussbaum | G06F 3/0447 |
| 10,252,640 | B2 * | 4/2019 | Cech | G08B 21/24 |
| 10,600,302 | B2 * | 3/2020 | Cech | B60N 2/002 |
| 10,615,194 | B1 * | 4/2020 | Iso-Ketola | G01L 1/142 |
| 10,908,034 | B2 * | 2/2021 | Moriura | G01L 5/221 |
| 11,299,044 | B2 * | 4/2022 | Tanabe | B60N 2/75 |
| 11,479,206 | B2 * | 10/2022 | Radunz | B60R 22/48 |
| 11,541,842 | B2 * | 1/2023 | Jaradi | B60R 22/34 |
| 11,571,155 | B2 * | 2/2023 | Ali | A61B 5/0816 |
| 2003/0009270 | A1 * | 1/2003 | Breed | B60N 2/0276 701/32.4 |
| 2003/0116362 | A1 * | 6/2003 | Breed | B60R 21/01554 177/144 |
| 2004/0080204 | A1 * | 4/2004 | Enomoto | B60R 21/01546 297/483 |
| 2006/0033507 | A1 * | 2/2006 | Gaumel | G01G 7/06 324/658 |
| 2008/0042409 | A1 * | 2/2008 | Breed | B60R 21/0134 701/45 |
| 2008/0319617 | A1 * | 12/2008 | Takemura | B60R 21/01546 701/45 |
| 2009/0033078 | A1 * | 2/2009 | Hawes | B60N 2/0025 280/735 |
| 2009/0140993 | A1 * | 6/2009 | Han | B60K 35/10 345/173 |
| 2011/0241860 | A1 * | 10/2011 | Andrews | B60R 21/0152 701/45 |
| 2012/0161777 | A1 * | 6/2012 | Nakagawa | B60R 21/0154 324/457 |
| 2013/0176100 | A1 * | 7/2013 | White | G08C 19/00 340/1.1 |
| 2015/0133804 | A1 * | 5/2015 | Sugiyama | B60N 2/64 600/509 |
| 2015/0229341 | A1 * | 8/2015 | Fung | A61B 5/0059 702/191 |
| 2015/0360643 | A1 | 12/2015 | Cech | |
| 2016/0349906 | A1 * | 12/2016 | Lee | G06F 3/04166 |
| 2017/0088096 | A1 * | 3/2017 | Luebbers | B60R 22/12 |
| 2017/0238174 | A1 * | 8/2017 | Cech | B60N 2/0026 455/411 |
| 2018/0087929 | A1 * | 3/2018 | Matsumura | G01D 5/24 |
| 2018/0326944 | A1 * | 11/2018 | Cech | G06V 20/593 |
| 2019/0009739 | A1 * | 1/2019 | Lisseman | G05D 1/0061 |
| 2019/0047441 | A1 * | 2/2019 | Wilson | B60N 2/0027 |
| 2019/0049267 | A1 * | 2/2019 | Huang | G01C 21/3697 |
| 2019/0073055 | A1 * | 3/2019 | Nakai | B32B 27/12 |
| 2019/0112734 | A1 * | 4/2019 | Podhajny | D03D 1/0082 |
| 2019/0168710 | A1 * | 6/2019 | Liau | B60R 21/01532 |
| 2019/0193676 | A1 * | 6/2019 | Thomas | B60R 22/18 |
| 2019/0226879 | A1 * | 7/2019 | Lakatos | G01V 3/08 |
| 2019/0282178 | A1 * | 9/2019 | Volosin | A61B 5/02405 |
| 2019/0391581 | A1 * | 12/2019 | Vardaro | A61B 5/02055 |
| 2020/0106437 | A1 * | 4/2020 | Iso-Ketola | H05K 1/0283 |
| 2020/0198465 | A1 * | 6/2020 | Tanabe | G08G 1/00 |
| 2020/0214566 | A1 * | 7/2020 | Allen | A61B 5/681 |
| 2020/0216079 | A1 * | 7/2020 | Mahajan | G05D 1/0061 |
| 2020/0269863 | A1 * | 8/2020 | Yanagi | B60W 10/18 |
| 2020/0375011 | A1 * | 11/2020 | Tsibulevskiy | H02J 7/00036 |
| 2020/0383622 | A1 * | 12/2020 | Ali | A61B 5/113 |
| 2021/0016683 | A1 * | 1/2021 | Balde | B60N 2/64 |
| 2021/0048894 | A1 * | 2/2021 | Wang | G06F 3/016 |
| 2021/0078447 | A1 * | 3/2021 | Lin | B60R 21/01542 |
| 2021/0206344 | A1 * | 7/2021 | George | B60R 21/01534 |
| 2021/0331644 | A1 * | 10/2021 | Radunz | B60R 22/48 |
| 2021/0354703 | A1 * | 11/2021 | Fairgrieve | B60W 40/08 |
| 2021/0402891 | A1 * | 12/2021 | Oommen | B60N 2/0035 |
| 2022/0111819 | A1 * | 4/2022 | Jaradi | B60R 22/48 |
| 2022/0306123 | A1 * | 9/2022 | Hanson | B60W 50/0098 |
| 2022/0324329 | A1 * | 10/2022 | Hanson | B60W 40/08 |
| 2023/0052474 | A1 * | 2/2023 | Rajanna | G01C 21/3697 |
| 2023/0106673 | A1 * | 4/2023 | Asghar | G08G 1/0112 382/104 |
| 2024/0138027 | A1 * | 4/2024 | Beska | B60N 2/5685 |
| 2024/0157853 | A1 * | 5/2024 | Kunz | B60N 2/0244 |

FOREIGN PATENT DOCUMENTS

| | | | |
|---|---|---|---|
| JP | 2002127871 A | | 5/2002 |
| JP | 2011-068206 A | | 4/2011 |
| JP | 2015-205578 A | | 11/2015 |
| WO | 2004-103782 A1 | | 12/2004 |
| WO | 2016-128478 A1 | | 8/2016 |
| WO | WO-2017017278 A1 * | 2/2017 | ....... B60R 21/01544 |

OTHER PUBLICATIONS

International Search Report and Written Opinion in PCT/US2021/052910. Mailed Jan. 25, 2022. 13 pages.

Office Action issued in corresponding German Application No. 11 2021 004 410.9, Jun. 26, 2024, 5 pages.

* cited by examiner

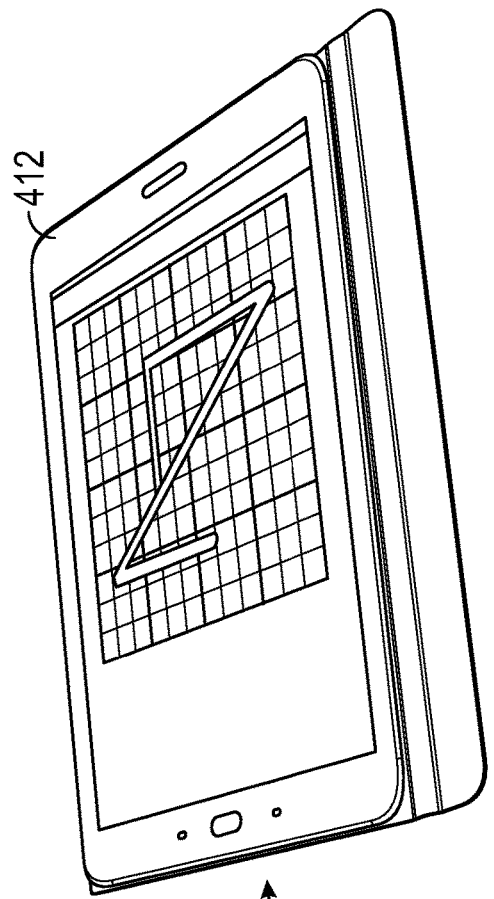
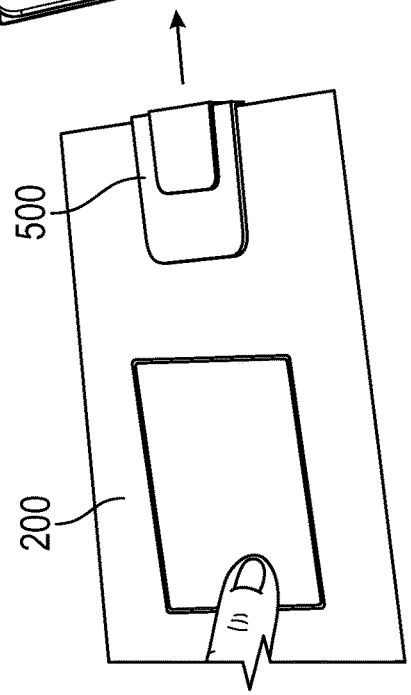
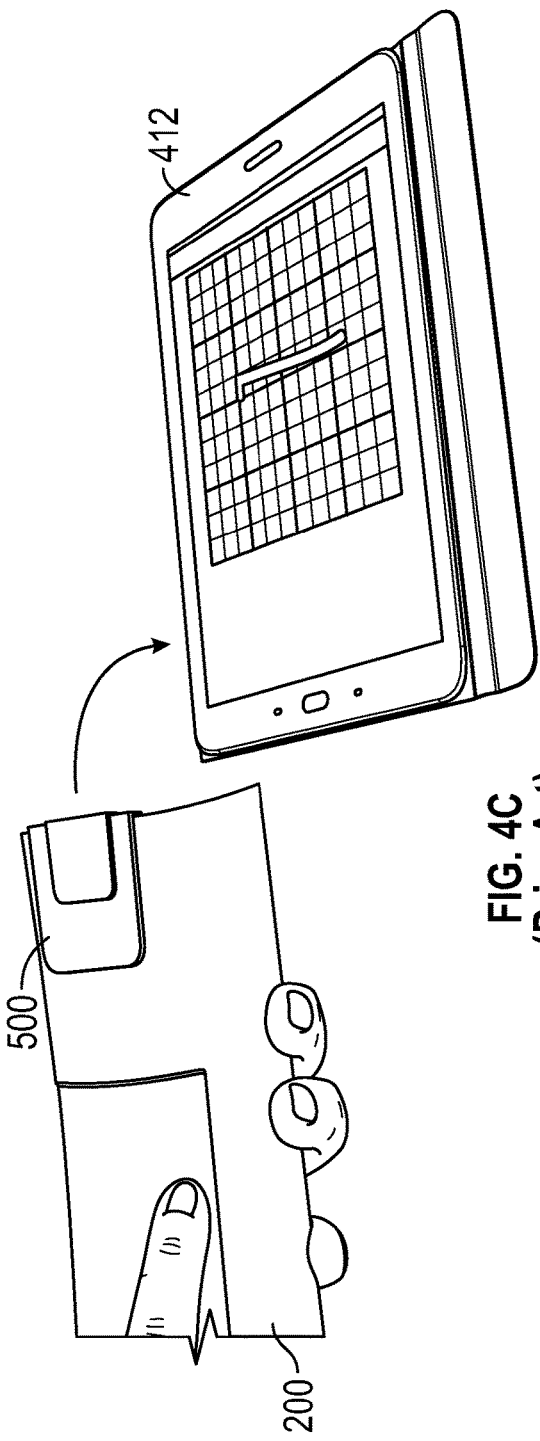
FIG. 4B (Prior Art)
FIG. 4C (Prior Art)

FORCE SENSING SEAT BELT SENSOR ASSEMBLY

CROSS REFERENCE TO RELATED APPLICATIONS

This application claims priority to and incorporates by reference U.S. Provisional Patent Application Ser. No. 63/085,645 filed on Sep. 30, 2020 and entitled Force Sensing Seat Belt Sensor Assembly.

TECHNICAL FIELD

The present disclosure relates to safety devices for passenger vehicles. In particular, the disclosure relates to a seat belt sensor assembly for sensing force. The seat belt sensor assembly may be used in any form of passenger vehicle, including, but not limited to, automobiles, personal recreational vehicles, aircraft, and spacecraft.

BACKGROUND

Seat belts have been used in vehicles for decades, providing one of the primary sources of safety for vehicle occupants involved in accidents. Traditionally, a commercial seat belt incorporates the majority of its technology in a retractor and/or pretensioner device. Alternatively, seat belts may be very simple safety belts without any advanced features, such as aircraft seat belts. Automated or "smart" sections of seat belt systems are currently limited to small, high resolution regions at one or more ends of the belt (e.g., monitoring regions of interest at the shoulder over which the belt rests and the hip on the opposite side).

Incorporation of a force sensor into a seat belt system, particularly by coupling a force sensor to a seat belt webbing, can provide for many advanced safety and human machine interface ("HMI") functions. For example, in one embodiment, the seat belt sensor system may detect that an occupant's respiration rate is above or below a threshold rate and provide a warning to the occupant. In another embodiment, the seat belt sensor system may allow for controlling vehicle systems, such as an infotainment system, via discrete activation zones of the seat belt sensor system. Therefore, by incorporating a force sensor into a seat belt system, safety and comfort features may be enhanced beyond those of a traditional seat belt system.

SUMMARY

A seat belt sensor assembly comprises a force sensor coupled to a seat belt webbing. The seat belt sensor assembly utilizes force readings from the force sensor indicating a force level above or below a predetermined threshold to determine if an action needs to be taken to control a vehicle system. Such vehicle systems could include, but are not limited to, an autonomous driving control system, an occupant health system, and a motorized seat belt retractor system. Controlling the vehicle systems could include, but is not limited to, sending audio, visual, and/or haptic warnings to vehicle occupants, including, in one embodiment, that the occupant's respiration rate is indicative of a dangerous health condition. The seat belt sensor assembly may be used in combination with a camera-based occupant monitoring system. In one embodiment, the occupant monitoring system can be used to selectively activate/deactivate discrete activation zones of the force sensor.

BRIEF DESCRIPTION OF THE DRAWINGS

FIG. 3B is a PRIOR ART perspective view of a set of electrodes forming respective sensing nodes within the multi-node force sensor of FIG. 3a.

FIG. 4B is a PRIOR ART perspective view of the force sensor of FIGS. 2a, 2b, 2c, 2d connected to an electronic control unit and a display computer and configured for touch sensor testing purposes as disclosed herein.

FIG. 4C is a PRIOR ART perspective view of the force sensor of FIGS. 2a, 2b, 2c, 2d, and 4b connected to an electronic control unit and a display computer and configured for touch sensor testing under conditions in which the force sensor is flexibly curved to a radius determined by manual manipulation for purposes as disclosed herein.

DETAILED DESCRIPTION

Overview

Figure 1:
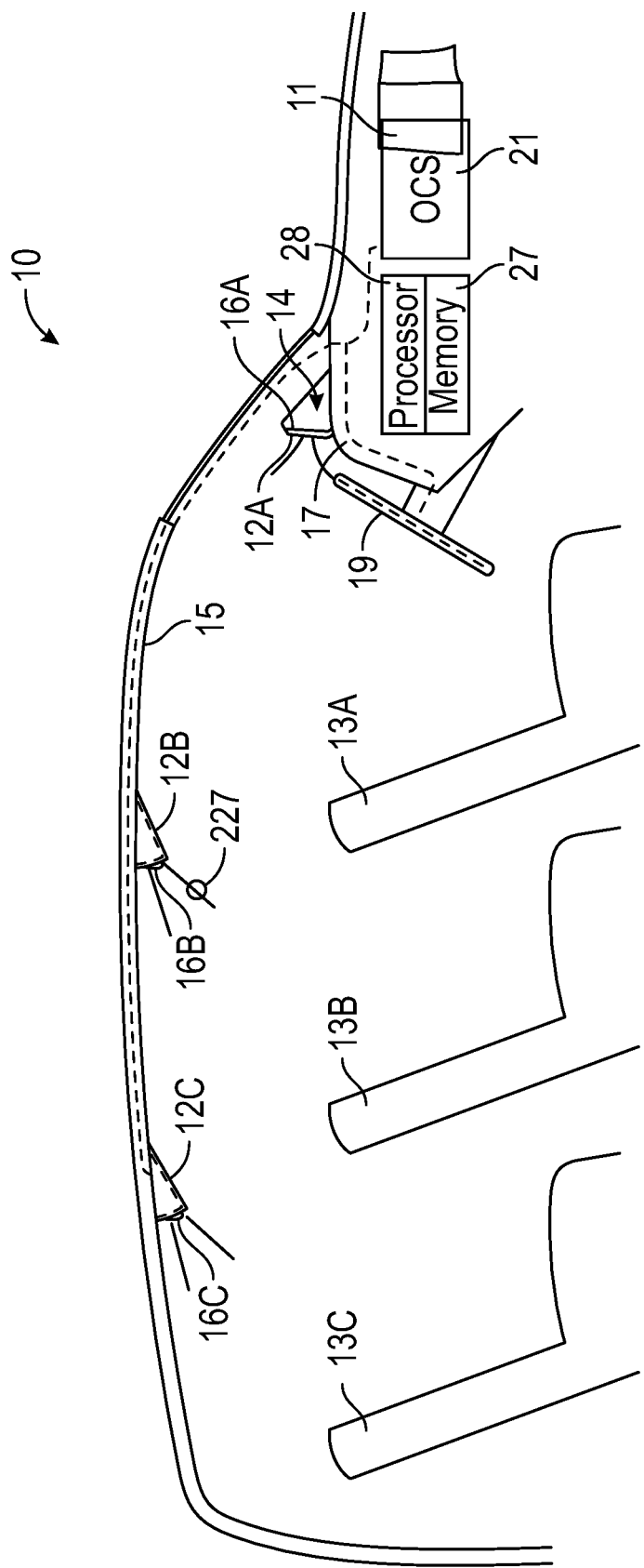
FIG. 1 is a perspective view of a cabin with a camera monitoring system having a field of view into the interior of the cabin in which force sensors may be installed as disclosed herein.

Embodiments of this disclosure are particularly, but not exclusively, useful in providing added functionality to structures that are already commonly found in vehicles, such as an automobile shown in FIG. 1. The term vehicle, however, is used according to its broadest plain meaning and includes, but is not limited to, any mobile machine used to transport occupants from one location to another (e.g., cars, trucks, boats, airplanes, amusement rides, carts, mass transit, farm equipment and the like). Vehicles are often equipped with safety devices, custom accessories, and electronic systems that make occupants more comfortable for using the vehicle in travel, work, or entertainment. Occupants interact with these components to operate the vehicle and comply with government safety regulations but also to operate numerous kinds of equipment in the vehicle that can be used for driving, riding, or simply enjoying entertainment within the vehicle. One non-limiting goal of this disclosure is to give structural features, already in the vehicle, additional functionality for the convenience of the occupants. This goal entails making inanimate structures within the vehicle smarter by incorporating sensing functions and communications capabilities within certain vehicle components. This disclosure includes discussions of force sensors relative to "supporting structures" within the vehicle. The term "supporting structures" includes, but is not limited to, vehicle occupants and vehicle components having a physical presence in contact with or in proximity to the force sensors such that the force sensors exhibit electrical and mechanical changes that are detected as described herein.

For example, currently, the primary method of occupant input to vehicle systems is primarily focused on the driver using steering wheel pushbuttons, driver and passenger infotainment pushbuttons and/or 2-D or 3-D touchscreens. A secondary and evolving method is for occupants to give human-machine interface ("HMI") inputs through voice assistants. These kinds of developments have elevated user control of the vehicle without occupying the driver's hands, which should be steering usually, and without limiting the driver's attention to important events occurring around them within the vehicle and outside the vehicle. Even so, the real estate available within vehicles is limited, and the steering assemblies and dashboard areas in common vehicle designs cannot provide all of the space necessary to install computers, hardware, mechanical devices, and network infrastructure that are necessary to achieve high levels of safe control over vehicle systems. The embodiments of this disclosure add devices, systems, and methods to control all aspects of the vehicle systems and operations from new vantage points that have never been utilized previously for smart, electronic monitoring and communication systems.

Additional functionality in vehicles, particularly from a communications perspective, are always facing new demands. For example, as automated driving and ride share services have evolved, vehicles have developed a transactional value that places more demands (and freedoms) on each occupant. For example, each individual occupant may have a different destination, be responsible for respective payments and may desire to be in direct control of their comfort options and audio-visual entertainment. Also, seat geometry may have new and more degrees of freedom and non-conventional configurations (e.g. campfire seating, facing backward, lying down, etc.) are becoming more commonplace in mass transit vehicles. To support these new degrees of freedom, the entire seat assembly may be reconfigured as an individual pod, complete with a network of sensors, data connections, and bi-directional telecommunications with external networks (i.e., vehicle infotainment systems, the internet, cloud services, wireless technologies and the like).

Of all the accessible real estate within a vehicle interior, one universally present but under-utilized space is a seat belt. Seat belts are not only a very important passive safety device for occupant safety, but they are readily accessible for manual manipulation without distracting a driver or impeding the driver's line of sight. Seat belts generally emanate from retractors placed in the vehicle pillars (B, C), so they also have sturdy and reliable anchor points within the vehicle for reliable operation. Seat belts are also prominent features during use by an occupant, so they provide surface space that is readily identifiable by machine vision systems included in a vehicle to monitor a driver and/or occupants.

After all, monitoring vehicle occupants will almost automatically include monitoring the seat belt. Accordingly, seat belt surfaces might be enhanced to improve proper belt use and belt positioning on occupant (e.g., confirming that the seat belt is properly fixed, determining if an occupant is moving, identifying hands and head orientation during vehicle use.)

In light of the above developments in vehicle engineering, embodiments of this disclosure include the integration of a flexible, stretchable sensor array into the seat belt webbing (e.g. adhered onto the webbing, laminated thereon, placed inside a webbing pocket, or laminated between webbing layers), such that the sensor array is composed to cover placement over the occupant chest and lap in a properly fitted seat belt. An electrode array can be configured into sensor elements of any desired size, shape and placement to support sensing occupant size, proper belt use, occupant movement and breathing. The electrode array may be considered an input array which can be used by the occupant through finger presses and gestures as an HMI input device. The sensor electrode array is connected to an electronic control unit integrated into the belt, seat or floor (or other vehicle location) to receive power and send/receive information to the vehicle.

The seat belt can also include visual/haptic actuators as needed to support the sensor and HMI functions, provide warnings, and to discern or even control occupant activities going on within the vehicle. Generally, this disclosure enables a force sensing seat belt, consisting of multiple capacitive elements of novel dielectric material, to be embedded within a sleeve to fit around the belt or to be implemented within a tubular belt, for the purpose of providing feedback to the vehicle about the forces applied to the seat belt. These forces may be the result of proper and/or improper uses of the belt as a safety device. This disclosure also explains using the seat belt as an interface to any number of peripheral systems to be controlled by sensing and measuring physical changes (kinetic, electromagnetic, and capacitive changes) around a sensor associated with the seat belt.

Accordingly, this disclosure expands the utility of the traditional seat belt yet still providing the safety features that have become the industry standard. In some embodiments, a capacitive element with one or more regions would be placed inside or on a seat belt, providing a direct relation between the capacitance sensed by the sensor and the force applied by the belt or onto the belt. This direct relation could be used for a variety of reasons, including enhanced safety, comfort, and convenience. Namely, this disclosure explicitly introduces the use of such a device to be used to control systems within the vehicle by providing an interface on the seat belt itself.

Including a capacitive sensor in the seat belt can be leveraged for a variety of enhanced features, both safety related and for occupant comfort and convenience. By including zones of higher spatial resolution across the belt, a small area for HMI interaction can be included to provide occupants the option to interface with various systems in a way that limits leaning towards the traditional HMI controls, and with sufficient training, could alleviate gazing away from the road for the driver. Some examples of systems to be controlled include but are not limited to seat belt tension, entertainment volume, changing radio stations/songs, selecting presets on the infotainment system, pulling up navigation or entertainment, answering a phone call, adjusting environmental settings (A/C, heater), etc.

Embodiments

Figure 2A:
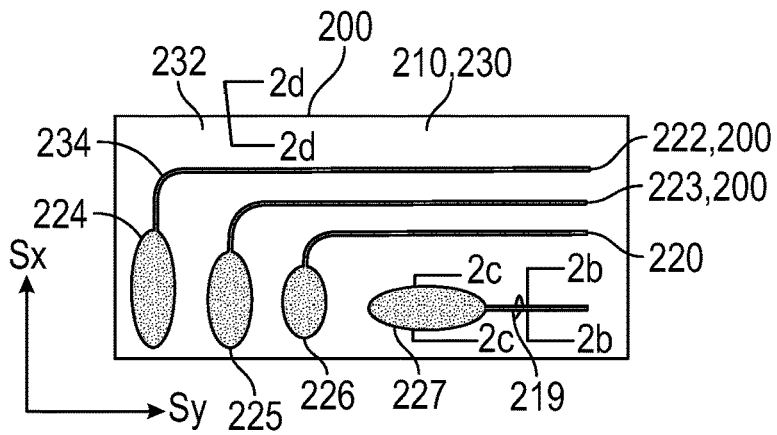
FIG. 2A shows, in a top view, a PRIOR ART multilayer capacitive structure configured as a force sensor 200 to provide capacitive sensor measurements according to embodiments of this disclosure.
Figure 2B:
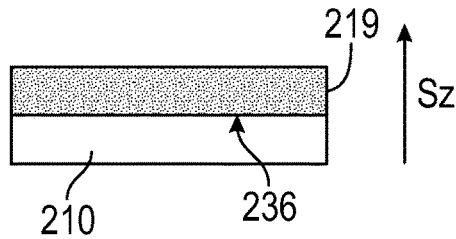
FIG. 2B shows, in a side cross section view, a PRIOR ART cross section of FIG. 2a taken across electrode 226 of force sensor 200, prior to adding a deformation layer 230 to the assembly, as discussed herein.
Figure 2C:
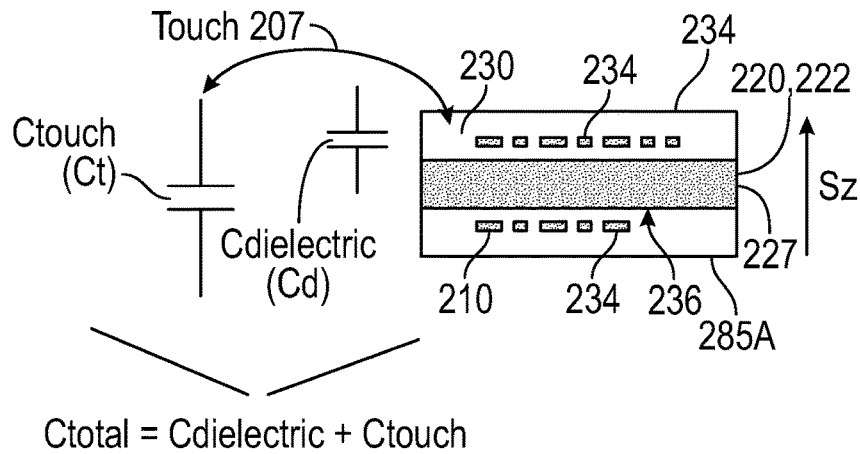
FIG. 2C shows, in a side view, a PRIOR ART cross section of FIG. 2a taken across electrode 226 of force sensor 200, after adding a deformation layer 230 to the assembly, as discussed herein.
Figure 2D:
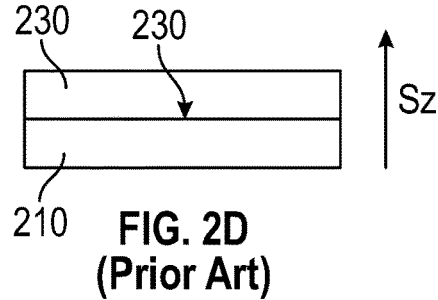
FIG. 2D shows, in a side view, a PRIOR ART cross section of FIG. 2a that does not include an electrode but does include a junction between a flexible substrate and a deformation layer as described herein.

One non-limiting example of a capacitive sensor available for use in example embodiments of this disclosure is shown in prior art FIGS. 2A, 2B, 2C, and 2D, originally shown in U.S. Patent Pub. No. 20200106437 currently assigned to an example manufacturer Forciot Oy (FORCIOT®). These different views of FIG. 2 show a flexible force sensor 200 configured to conform to shapes of supporting structures in a vehicle, such as but not limited to, seat belts. The flexible force sensor 200 may include a force sensing electrode 224, 225, 226, 227 positioned between a flexible substrate 210 and a deformable dielectric layer 230, the force sensing electrode defining a respective capacitive measurement area 234 along the Sz direction of FIG. 2C through the flexible force sensor. The flexible force sensor is positioned within a vehicle to detect changes in total capacitance at the capacitive measurement area. As illustrated in FIG. 2C, total capacitance is considered for each capacitive measurement area 234, also referred to as discrete activation zones 234, having a perimeter defined by the respective electrodes 224, 225, 226, 227 and extending through the thickness in the Sz direction of the body of the sensor 200.

The sensor 200 of FIGS. 2A-2D can be used as an active sensor upon installation because each of the electrodes 224, 225, 226 connect to a microcontroller or other computing device via respective conductors 220, 222, 223. These conductors can be used to deliver electronic pulses to the electrodes to initiate electromagnetic responses through the sensor. In operation, total capacitance Ctotal at each capacitive measurement area 234 through the sensor 200 would include dielectric capacitance through the body of the sensor 200, as modulated by outside touches, such as touches 207 with a vehicle occupant's finger. The touches 207 initiate respective touch capacitances Ct in parallel with the dielectric capacitance (Cd) of the sensor 200. With this construction and capacitive phenomena in the sensor 200, the microcontroller and associated systems can use capacitance data to determine activities around the sensor, whether the activities include pressure on the sensor, touches, or other physical manipulation about the capacitive measurement areas 234 (schematically showing Ctotal as two imaginary capacitor plates within the body of the sensor 200 on opposite sides of one electrode 227).

Figure 3A:
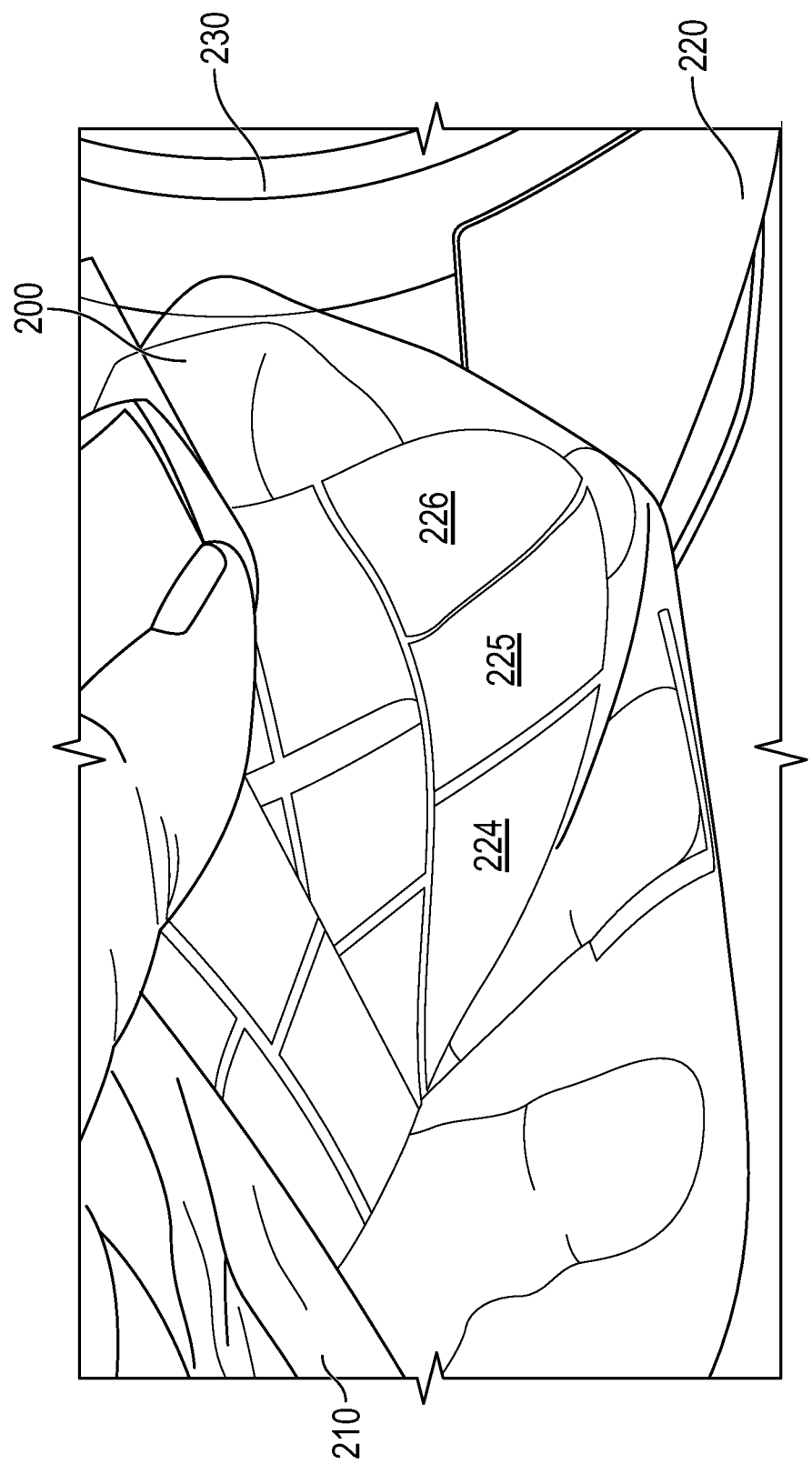
FIG. 3A is a PRIOR ART perspective view of a flexible and stretchable multilayer capacitive structure configured as a multi-node force sensor for use in a vehicle as described herein.
Figure 3B:
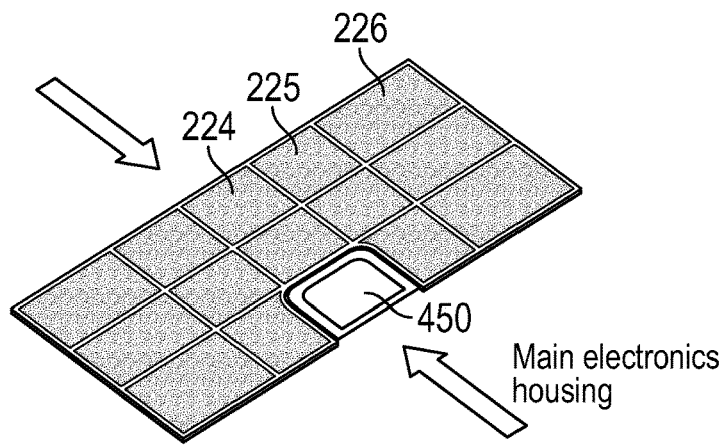

As noted above, the sensor 200 may be configured with a thin film or sheet that is flexible, bendable, stretchable and generally resilient enough to fit numerous installation requirements. One non-limiting example of a flexible force sensor of this disclosure is shown in prior art FIGS. 3A, 3B, 3C, 3D as marketed, for example and without limiting this disclosure to any one embodiment, by FORCIOT®. In FIG. 3A, the force sensor 200 is a clear sheet that is bendable to a particular radius R-bend. This sheet also includes sufficient flexibility, stretching resilience, and malleability to conform to numerous structures within a vehicle to provide sensing opportunities therein. As illustrated in FIGS. 2 and 3, one sensor 200 of this disclosure is a capacitive sensor in which a flexible substrate 210 supports electrodes 224, 225, 226 and is covered with a deformable dielectric layer 230. The multilayer structure exhibits notable changes in capacitance as described herein that are measured by associated electronics connected to the sensor 200. The electrodes 224, 225, 226 may be applied to the flexible substrate 210 by methods including sputtering, deposition, printing and other processes. In some embodiments, the electrodes also exhibit flexibility and resilient stretching characteristics similar to the flexible substrate 210 and the deformable dielectric layer 230 for compatibility in construction and uses.

Figure 3C:
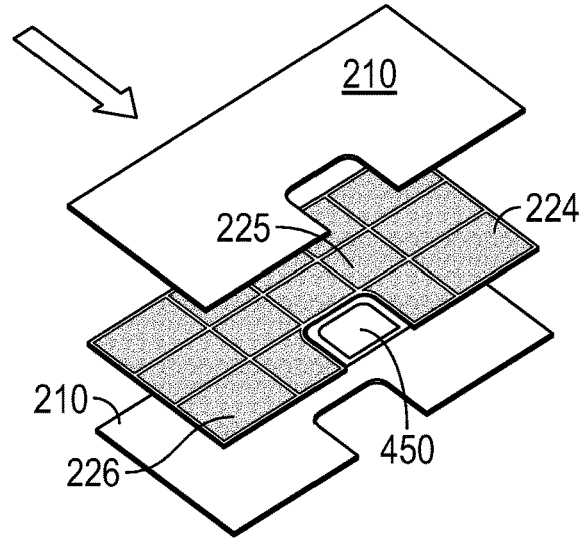
FIG. 3C is a PRIOR ART exploded perspective view of a multi-node force sensor having a flexible substrate layer, a pressure sensor layer of electrodes, and a deformation layer as disclosed herein.
Figure 3D:
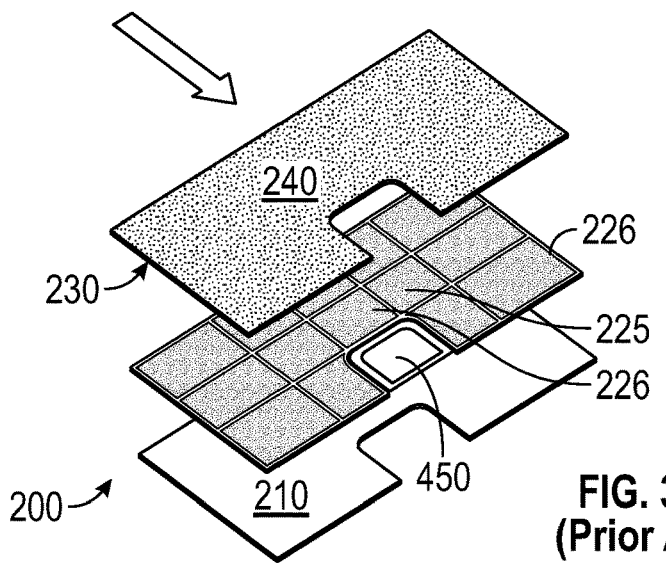
FIG. 3D is a PRIOR ART exploded perspective view of a multi-node force sensor having a flexible substrate layer, a pressure sensor layer of electrodes, a deformation layer, and a grounding layer as disclosed herein.

The construction of an example flexible force sensor 200, as shown herein, may include layered portions in which an array of printed electrodes 224, 225, 226, etc. are formed and attached along with a computing device and associated electronics 450 on a flexible substrate 210. FIG. 3C illustrates the addition of a deformable dielectric layer 230, and optionally, in FIG. 3D, a grounding layer 240 may be coated onto the deformable dielectric layer 230. The grounding layer 240 may be a conductive layer connected to a ground of an electronic control unit. Some embodiments may omit the separate grounding layer 240, opting instead for a floating ground for the electrodes, depending on the installation adjacent thereto. The grounding connections for a plurality of force sensors in a single installation may be the same or differentiated according to the needs at hand, wherein the common ground of an electronic control unit 450 is available as is a ground provided to earth by the body of the vehicle.

Figure 4A:
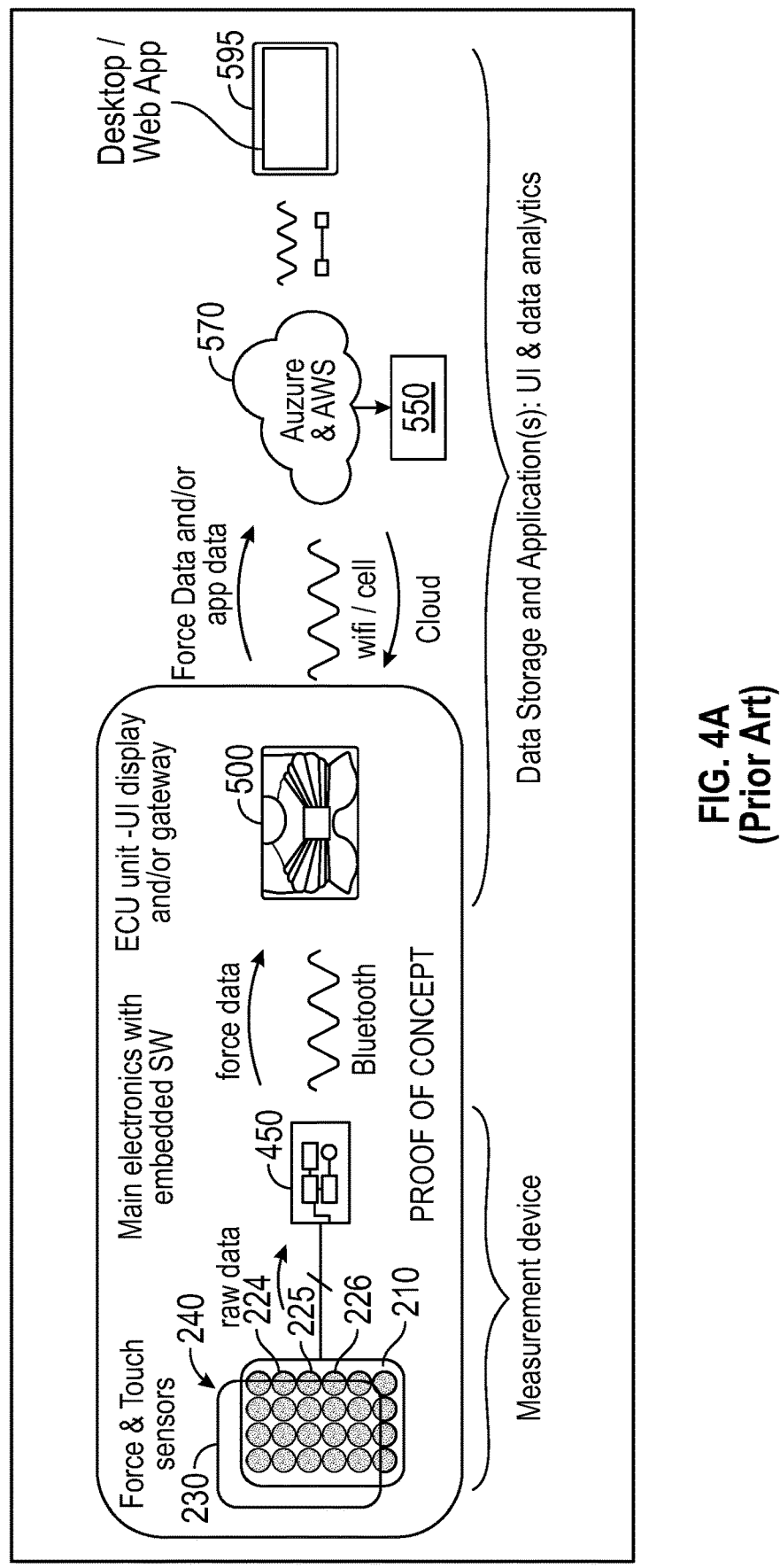
FIG. 4A is a PRIOR ART schematic illustration of a sensor system connected to peripheral electronics and networks as disclosed herein.
Figure 5:
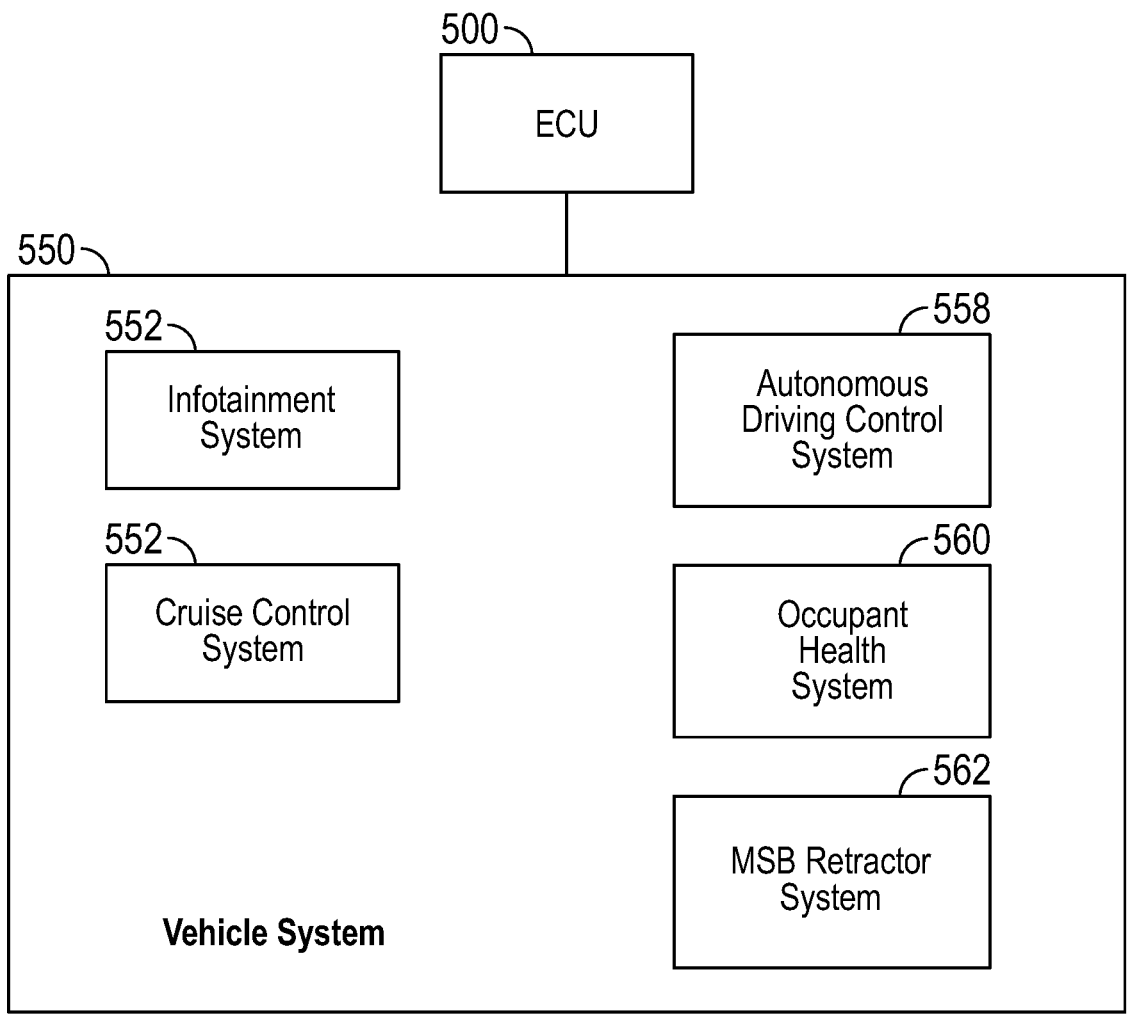
FIG. 5 is a schematic illustration of an electronic control unit (ECU) in communication with a force sensor and corresponding sensor electronics for transmitting data to vehicle systems as disclosed herein.

FIGS. 4A, 4B, 4C illustrate additional details of a representative, non-limiting force sensor (e.g., a sensor known to be marketed by FORCIOT®), FIG. 4A shows that the flexible force sensors 200 described herein may be part of a network of communicating devices. In one embodiment, the microcontroller 450 of the sensor 200 may be connected to a vehicle electronic control unit 500 for more complex analysis of signals from the sensors 200 (i.e., detecting changes in capacitance). The electronic control unit 500 may be further connected by WiFi, Bluetooth, and other communications protocols to cloud operations, other computers 595, and/or vehicle computer and control systems 550. With the sensors 200 in place in a vehicle, the user may be able to manually manipulate the sensors 200 with touch as shown in FIG. 4B and achieve a recognizable change in capacitance at the sensor. The change in capacitance may be used for computational purposes, control purposes, or graphical display 412 as shown in similar examples of FIGS. 4B and 4C. It is notable that in FIG. 4C, bending or rolling the sensor 200 provides accurate sensing capabilities, illustrating that the flexible substrate sensor operates correctly even when bent for a given installation. FIG. 5 is another flow chart illustrating that the sensors 200 may be used to communicate, via an electronic control unit 500, with numerous vehicle control systems 550, including, but not limited to an infotainment system 552, cruise control system 556, autonomous driving control system 558, occupant health system 560, or motorized seat belt retractor system 562.

Figure 6A:
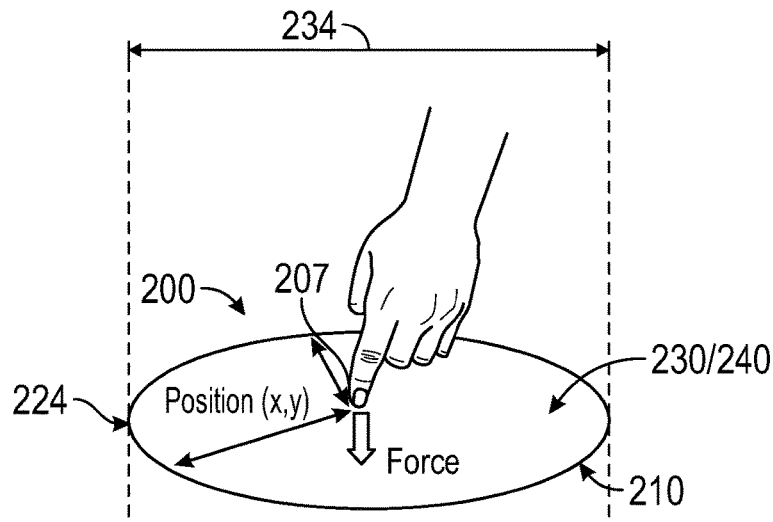
FIG. 6A is a schematic illustration of a finger touching one of the nodes of the force sensor of this disclosure.
Figure 6B:
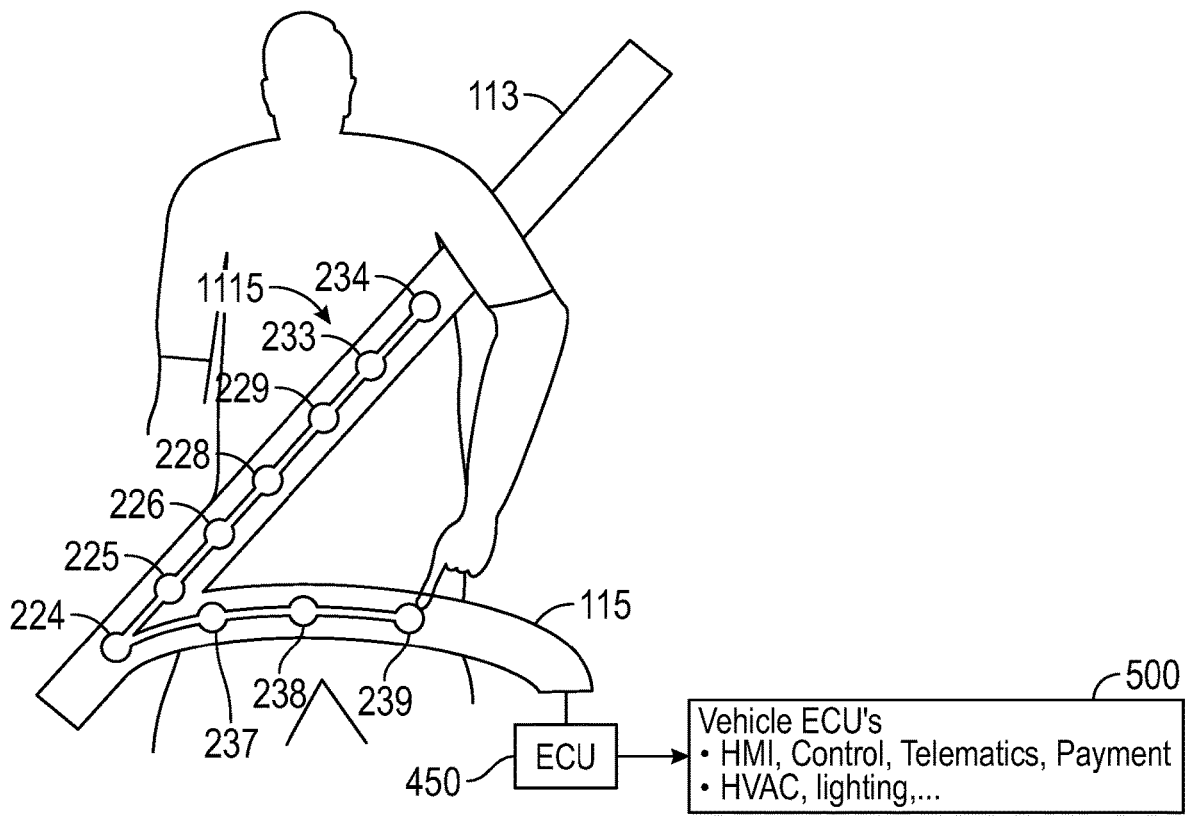
FIG. 6B is a schematic illustration of a force sensor assembly configured for use with a seat belt in which the nodes of the force sensor are in data communication with other peripheral systems as disclosed herein.

The flexible force sensor 200 of this disclosure may be suitable to detect changes in the capacitive behavior of the sensor, whether the change in capacitance is caused by pressure (e.g., compression of the sensor), stretching and tension on the sensor, or touch and other manual manipulations on or near the sensor. In fact, the sensor 200 may be sufficiently sensitive to have changes in capacitance detected and communicated to various control systems even when the kinetic, or mechanical changes, are proximate a flexible force sensor system but actually directly located in supporting structures connected to the sensors. FIGS. 6A and 6B show two examples of different opportunities available because the flexible force sensor 200 is particularly adept at sensing both mechanical forces on inanimate objects and touch forces caused by humans interacting with the sensors. In FIG. 6A, a touch 207 exerts a force on to the force sensor 200, and a connected electronic control unit detects the capacitive changes occurring at the force sensor 200. In FIG. 6A, the touch is on one of the electrodes 224, defining a perimeter of a capacitive measurement area 234 extending from one side to the other side of the electrode perimeter and through the body of the force sensor 200 along the Sz axis as shown in FIG. 2C (i.e., a change in capacitance can be measured from the flexible substrate 210 and also from the deformable dielectric layer 230). The ECU detects the capacitive changes due to the touch of FIG. 6A and maps the touch to a corresponding location on the touch sensor. In other words, the controller may include software that maps locations on a supporting structure, such as a seat belt according to known electrode positions that a force sensor places thereon.

FIG. 6B illustrates at least one use for the capacitive measurements available via a flexible force sensor 200 by installing a plurality of force sensors 200 as a detection or monitoring system. In one embodiment, a number of force sensors 200 provide corresponding electrodes 224, 225, 226, 227, 228, 229, 233, 234 on a first part of a seat belt 1115, such as a shoulder strap 113. A different force sensor may provide electrodes 237, 238, 239 on a lap belt portion 115 of a seat belt assembly. These sensors and associated electrodes (with corresponding capacitive measurement areas 234, also referred to as discrete activation zones) are available to provide data regarding capacitive changes at the sensor. This data can be transmitted to associated computers for analysis and use in vehicle control operations.

Figure 7A:
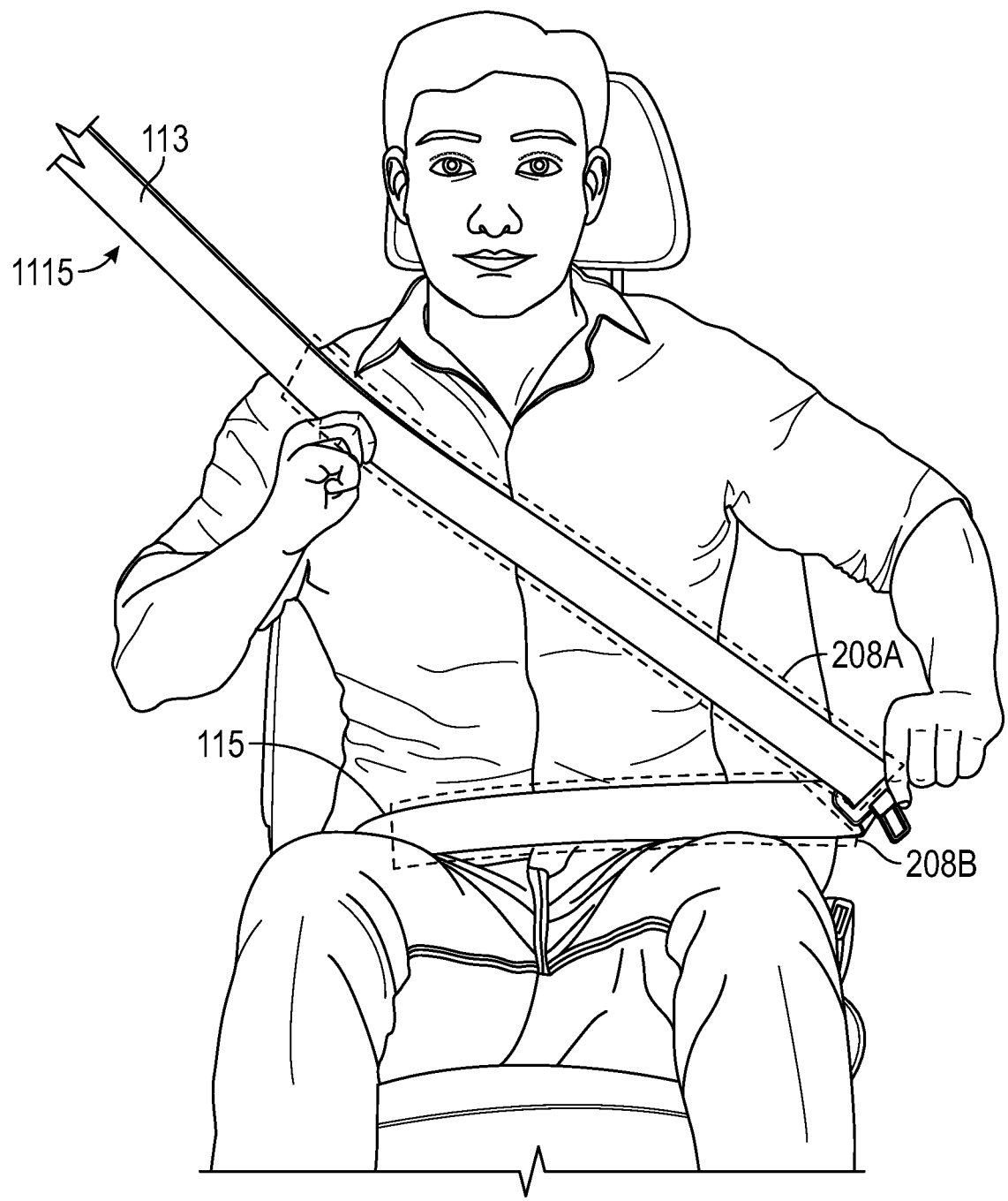
FIG. 7A is a front plan view of a vehicle seat belt configured with surface placement for at least one force sensor according to this disclosure.
Figure 7B:
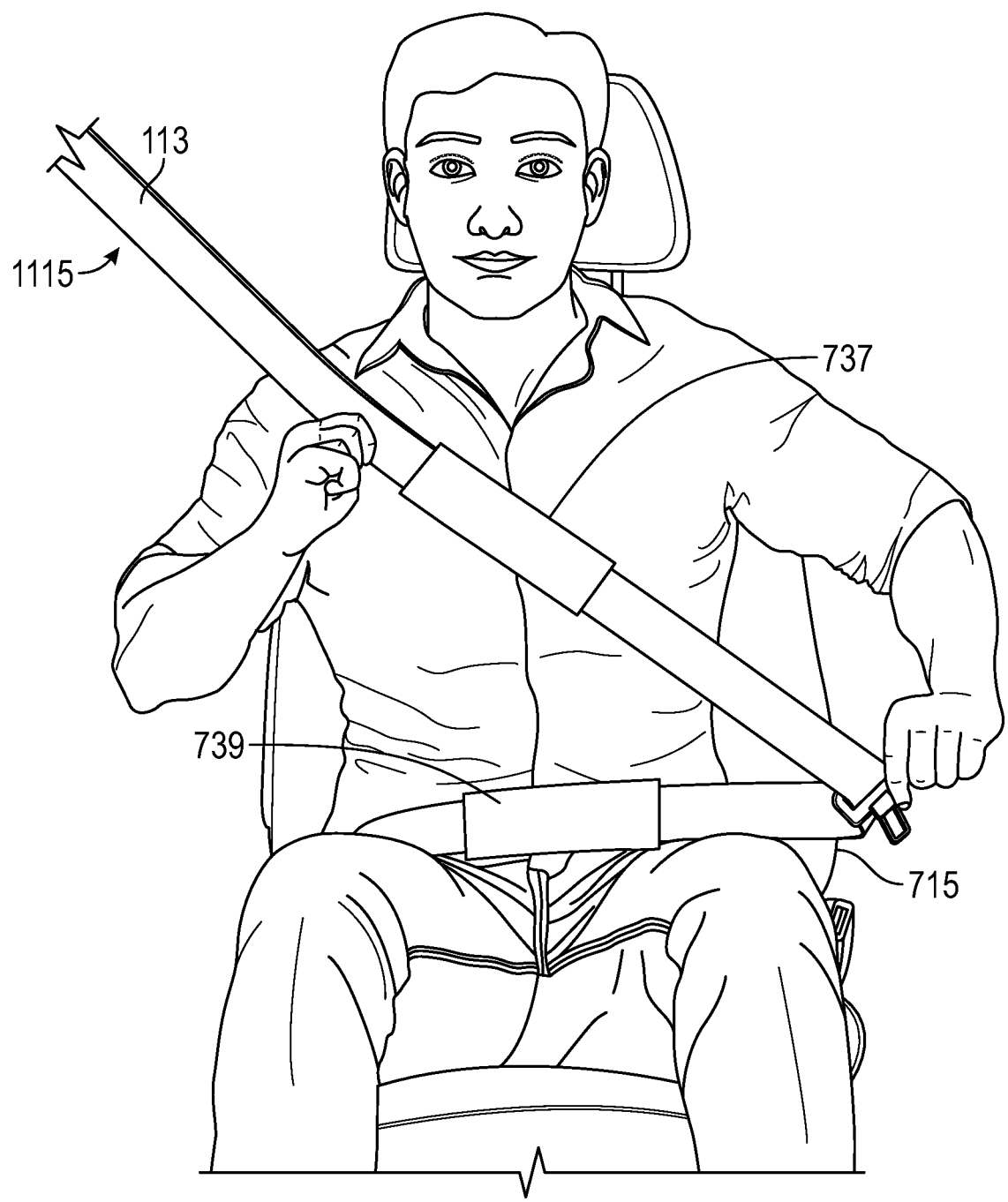
FIG. 7B is a schematic view of schematic drawing illustrating example levels of pressure applied to the vehicle seat belt as measured by the force sensors placed in FIG. 7A.

FIGS. 7A and 7B illustrate how a seat belt assembly, including a seat belt 1115 a shoulder belt 113 portion and a lap belt 115 portion having designated areas 208A, 208B that are available for sensor placement, converting the seat belt from a simple mechanical device to a computerized system of data collection. FIG. 7B shows regions of the seat belt connected to respective flexible force sensors 737, 739 available for capacitive measurements to track pressure/compressive forces on the sensor, particularly in regard to the deformable dielectric layer 230 of a sensor. The same force sensors are likewise available for use in sensing and tracking different touches, pinches, sliding motions, and gestures on and around the seat belt portions 713, 715. In one example operation, the total capacitance at each capacitive measurement area of the force sensor, defined by respective electrodes 224, 225, 226, can be tracked electronically to detect changes in the capacitance values that indicate a touch on the surface of the electrodes, a touch on a different side of the deformable dielectric layer, compression of the deformable dielectric layer, or a series of swipes and gestures formed across an area of the seat belt portions. All of these physical changes cause corresponding capacitance changes which are susceptible to tracking by connected electronics. In this system, an array of electrodes in a respective force sensor may be monitored over time to gather communication data that correlates to locations of touches, pinches, and other manual manipulations of a region on a seat belt. For example, the user may touch and slide that touch over a seat belt, and certain electrodes will experience a change in capacitance at the capacitive measurement areas, allowing the electronic control unit to map and track a human machine interface using the capacitive measurements. There are a number of different manual manipulations that are detectable and trackable with the flexible force sensor 200 of this disclosure. Certain regions of a seat belt may have respective flexible force sensors 200 arranged in respective, numerous orientations to sense a user's command. The commands may be coded into a touch, touch and release, a touch and glide over certain electrodes (i.e., communicating with gestures and finger drawings proximate the electrodes), a pinch for a certain period time, a pinch and swipe function, or any other series of manual interactions with a seat belt assembly and an associated system of flexible force sensors providing capacitive response tracking data. The commands may originate from either an inner side 1207 of the seat belt closest to an occupant or an exposed outer side 1205 of a seat belt distal from the occupant.

Figure 16:
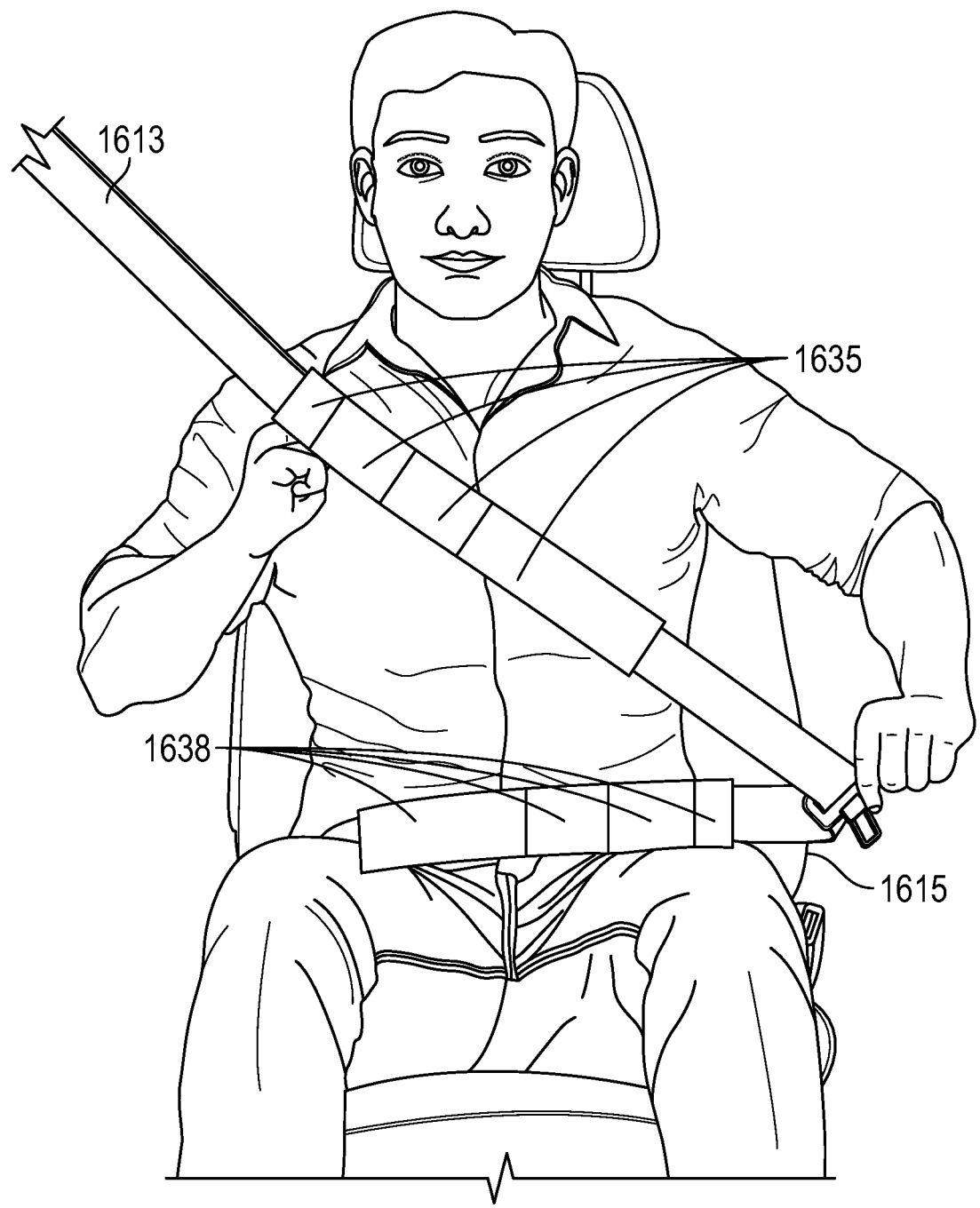
FIG. 16 is front perspective view of a seat belt assembly in a vehicle with force sensors of this disclosure positioned on a shoulder belt and a lap belt for pressure measurements relative to a vehicle occupant's body.
Figure 17A:
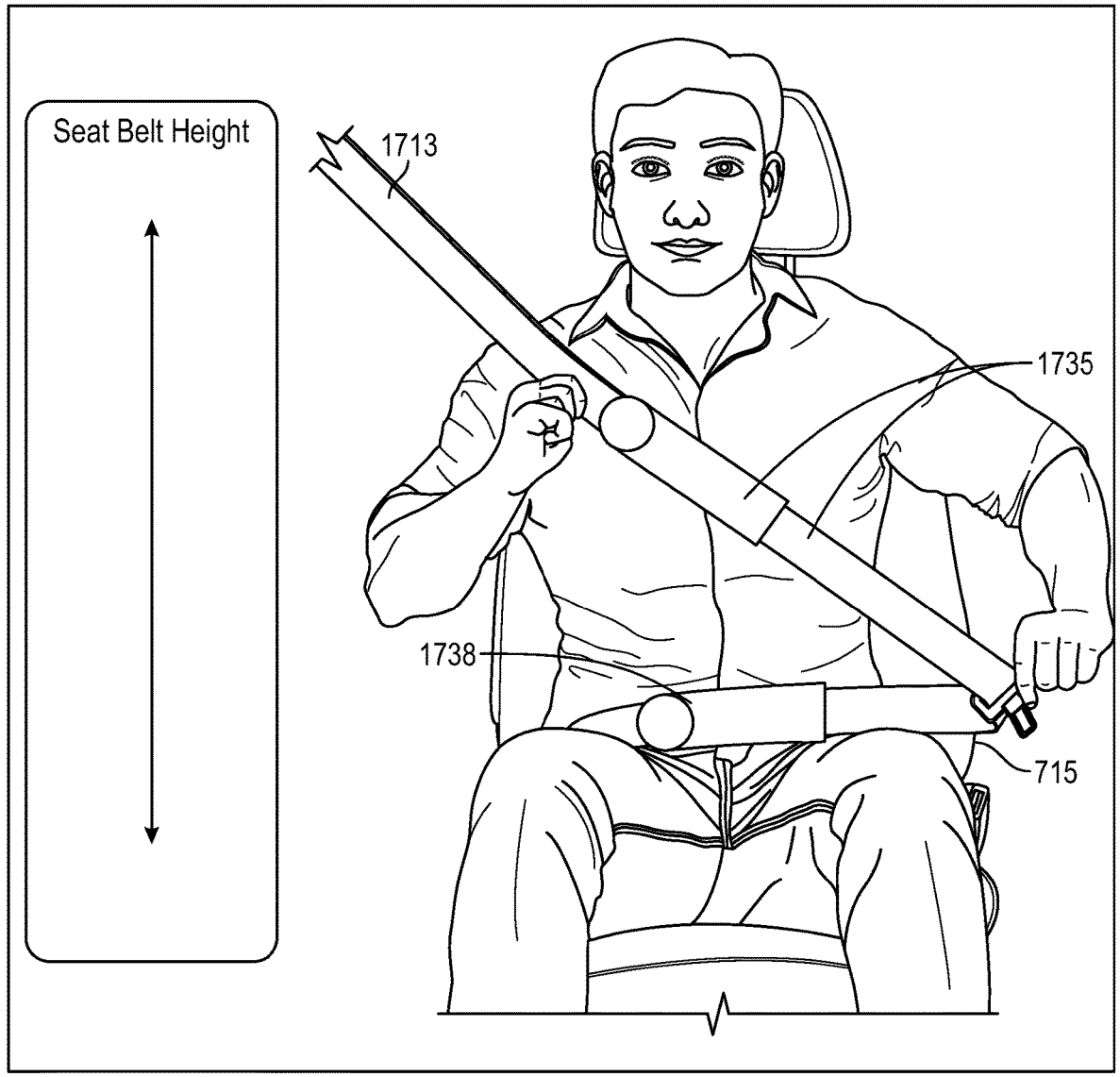
FIG. 17A is a schematic illustration of areas along a seat belt webbing associated with the force sensors of this disclosure and providing respective regions for inputs of varying types and pressure magnitudes along the seat belt assembly of FIG. 16.
Figure 17B:
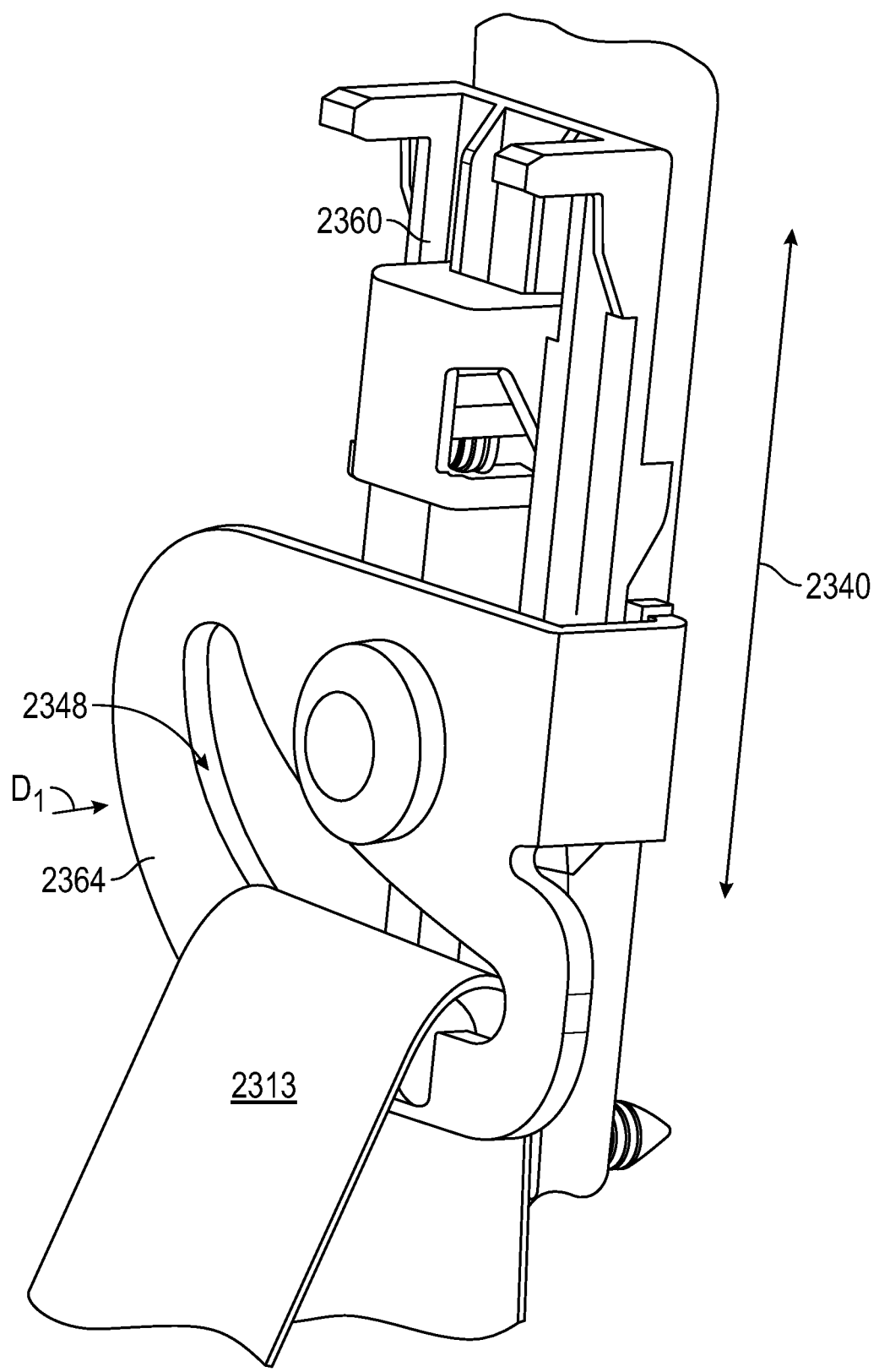
FIG. 17B is a schematic illustration of a D-ring structure in an automated seat belt D-ring position adjuster having variable height options along a pillar in the vehicle.

One notable characteristic of seat belt assemblies outfitted with the flexible force sensors 200 of this disclosure is the use of multiple sensors at distinctive orientations relative to a vehicle user and/or a supporting structure, such as a seat belt 1115 or parts of a seat belt webbing 113, 115, in the vehicle. Depending on the physical characteristic of interest in the vehicle or its occupants, the flexible force sensors 200 may be installed to not only conform to the variable shapes of seat belts in and out of operation with a user but also oriented in customized ways to provide the best detection of changes in capacitance for the parameter of interest. For example, in FIGS. 8-15, seat belt configurations may include the force sensors 200, 800, 900, 1000 of this disclosure turned to position the electrodes 224, 225, 226 inward or outward relative to inner faces 1207 and exposed faces 1205 of a seat belt. These different orientations may be mixed and matched at different points along a shoulder belt 113, 813, 913, 1013 and/or along a lap belt 115, 815, 915, 1015 of a seat belt 1115 depending on whether the goal is to determine a body position of a vehicle occupant engaging the seat belt, make touch surfaces accessible for a human machine interface on either an exposed side or an inner side of the seat belt, or possibly to track positions of different supporting structures near the sensors. An orientation of the flexible substrate 210, the electrodes 224, 225, 226, and the deformable dielectric layer 230, relative to at least one respective supporting structure in the vehicle, is adapted to detect the changes in total capacitance in response to physical positions of a respective supporting structure. As shown in FIGS. 16 and 17, depending on the orientation of the sensor, some embodiments may include using the force sensors to detect a vehicle user's body 1600 exerting pressure on the sensors at different positions 1635, 1638 along the seat belt webbing 1613, 1615. FIG. 17 illustrates that certain pressure data, gathered by detecting changes in capacitance at the flexible force sensors 200, may be used to ensure proper use of the seat belt for safety purposes. The highlighted regions 1735, 1738 may be configured to determine pressure readings indicating proper seat belt tension and position, or improper use of the seat belt. In the example of FIG. 17A, the height of an automated seat belt D-ring position adjuster, having variable height options along a pillar in the vehicle, can be identified and adjusted from pressure readings taken from force sensors 200 along the appropriate regions 1735, 1738 of the seat belt assembly. This data, received by an electronic control system and associated automation hardware, may be used to move a position of the automated seat belt D-ring position adjuster either up or down (or any required direction) as necessary for proper seat belt placement relative to a user's body. FIG. 17B illustrates that the D-ring 2364 receives a seat belt 2313 through an opening 2348 to stabilize the seat belt and maximize protection when in use. The height and body type of an occupant is indicated by detecting forces, such as pressure levels and touches on the seat belt webbing in and around the highlighted regions of FIG. 17A. Capacitive changes at these regions, detected by flexible force sensors 200, can provide ranges of force and pressure values along a length of the seat belt webbing to indicate when proper seat belt height 2340 has been achieved at the D ring of FIG. 17B.

The supporting structures in which force sensors, such as those described herein are used may be selected from the group consisting of vehicle occupants, vehicle seats, vehicle floorboards, seat belt webbings, seat belt hardware assemblies, and child restraint seats, among others.

In some embodiments shown in FIGS. 11-15, the supporting structure connected to the force sensors is a seat belt webbing 1116 comprising an exposed face 1117 and an inner face 1119, and wherein the flexible substrate 210 of the force sensor 200 is directly adjacent the inner face 1119, and a deformable dielectric layer 230 is between an electrode 227 and the exposed face 1117 of the seat belt webbing 1116. With this arrangement, the seat belt 1115 is a supporting structure providing options for which face of the seat belt is optimum for placing the sensor thereon and achieving the best readings.

In other embodiments of this disclosure, a vehicle sensor assembly may include, as described herein, a flexible force sensor 200 configured to conform to shapes of supporting structures in a vehicle. The supporting structures may be a number of different components in a vehicle or may be an occupant interacting and positioned proximately to those vehicle components. Similar to previously described embodiments, a plurality of force sensing electrodes 224, 225, 226 may be positioned between a flexible substrate 210 and a deformable dielectric layer 230, the force sensing electrodes 224, 225, 226 defining respective capacitive measurement areas 234 through a particular flexible force sensor 200. The flexible force sensor 200 is positioned within a vehicle to detect changes in total capacitance (Ctotal) at the capacitive measurement areas. The capacitive measurement areas 234 are generally of a similar perimeter as force sensing electrodes 224, 225, 226, and the capacitance as well as changes in capacitance may be detected on either side of a force sensor 200, depending on the supporting structures, the parameters being considered, and the uses at hand. The capacitive measurement areas 234 on the flexible force sensor 200 are configured to exhibit changes in the total capacitance due to a dielectric capacitance, Cd, in the deformable dielectric layer and a touch capacitance Ct between and among the flexible substrate 210, the dielectric area 230, and optionally a ground layer 240. An orientation of the deformable dielectric layer 230 and the force sensing electrodes 224, 225, 226, relative to a respective supporting structure in the vehicle, is adapted to provide the total capacitance (Ctotal) values to respective vehicle control systems. In some embodiments, the changes in the dielectric capacitance (Cd) reflect compression of the deformable dielectric layer 230. The compression of the deformable dielectric layer 230 indicates a pinching operation (such as manually pinching a portion of the seat belt along the seat belt webbing 1116) by a vehicle occupant, wherein the pinching operation correlates to a data communication to at least one of the vehicle systems. For example, as noted above, the force sensor placement along a seat belt 1115 may be mapped in computer memory, and capacitive changes at each electrode may correspond to respective pre-programmed functions tied to an overall vehicle control system, as shown in FIG. 5. In other configurations, changes in the touch capacitance reflect a manual touch 207 on an electrode side 285A of the flexible force sensor 200 proximate either the exposed side 1117 or the inner side 1119 of a seat belt. In any event, the changes in the touch capacitance and the dielectric capacitance are configured as a human machine interface with an electronic control unit.

In addition to using touch forces to communicate with an electronic control unit, the capacitive measurement areas of the flexible force sensor exhibit a change in the total capacitance due to compressive forces on the flexible force sensor 200. The compressive forces may originate from pairs of supporting structures in the vehicle on opposite sides of the flexible force sensor 200, and changes in total capacitance from the compressive forces are transmitted in data communications from the force sensing electrodes to the electronic control unit. The electronic control unit converts the changes in total capacitance to pressure values exerted at each of the capacitive measurement areas. As noted above, the physical objects delivering forces to the sensors may include both human body parts and inanimate components inside a vehicle cabin. These physical objects are referred to, without limiting this disclosure, as supporting structures in sufficient physical proximity to the force sensors to yield detectable changes in capacitance at the electrodes 224, 225, 226, 227 of FIG. 2A. The physical proximity may induce a touch, a pinching, a compression, a stretching, or other direct contacts with the force sensors. In other embodiments, merely approaching the force sensors at close proximity, with or without physical contact, with a finger or other conductive object may also yield detectable changes in capacitance that are recorded for use by a computer connected to the sensor assembly. The computer may receive measurement of magnitude and position of the forces in the embodiments of this disclosure.

Figure 12:
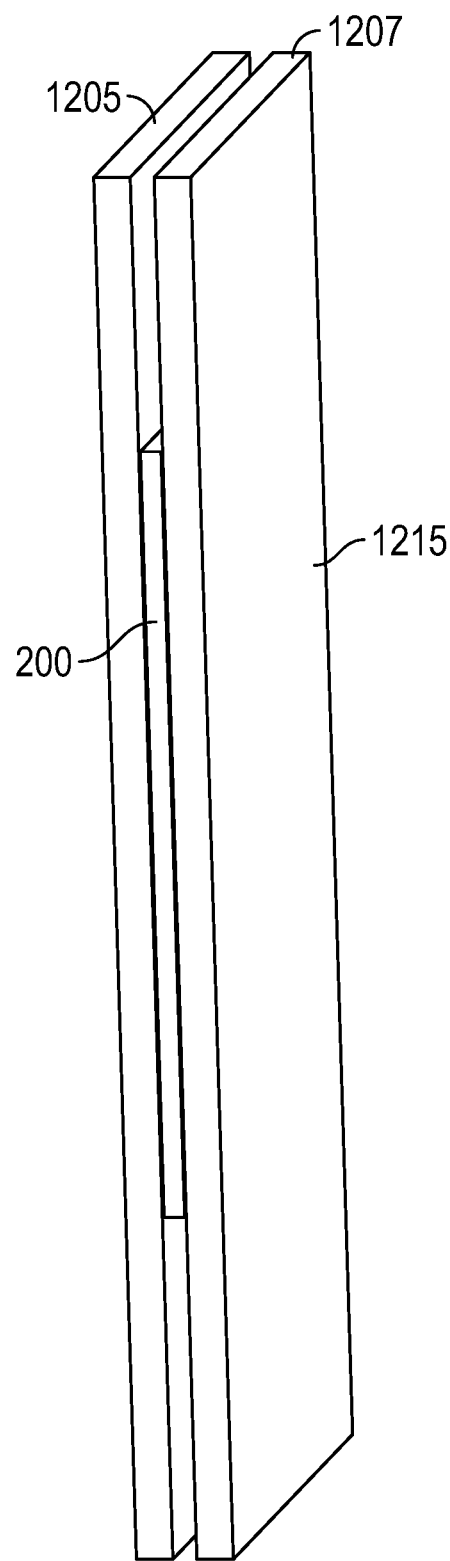
FIG. 12 is a perspective view of the force sensor laminated between two layers of seat belt webbing.

In one embodiment shown in FIG. 12, one pair of the supporting structures may be an exposed side 1205 and an inner side 1207 of a seat belt webbing 1215. This embodiment is configured to apply the compressive forces to the flexible force sensor 200 when used by a vehicle occupant, and the compressive forces having varying magnitudes across the flexible force sensor 200. The faces of the seat belt webbing 1215 essentially sandwich the force sensor 200, with the electrode closest to the appropriate face for the use at hand.

Figure 13:
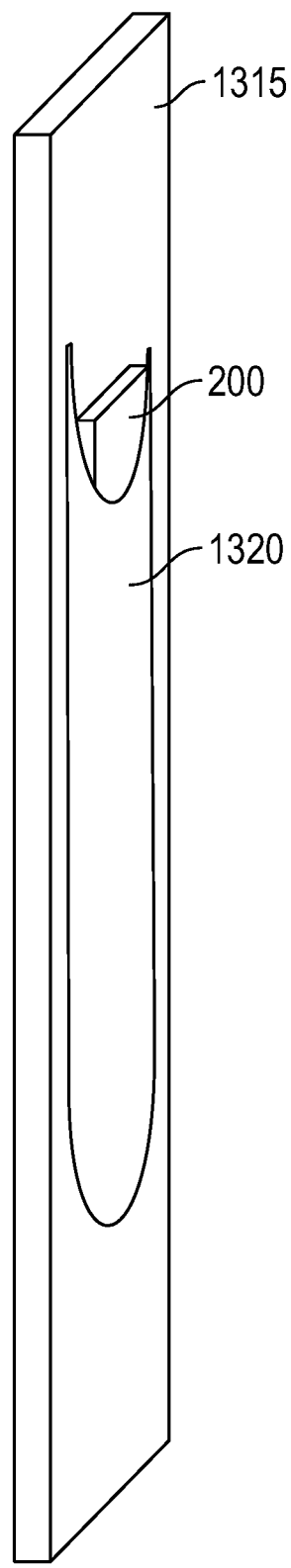
FIG. 13 is a perspective view of the force sensor positioned within a seat belt webbing pocket.
Figure 14:
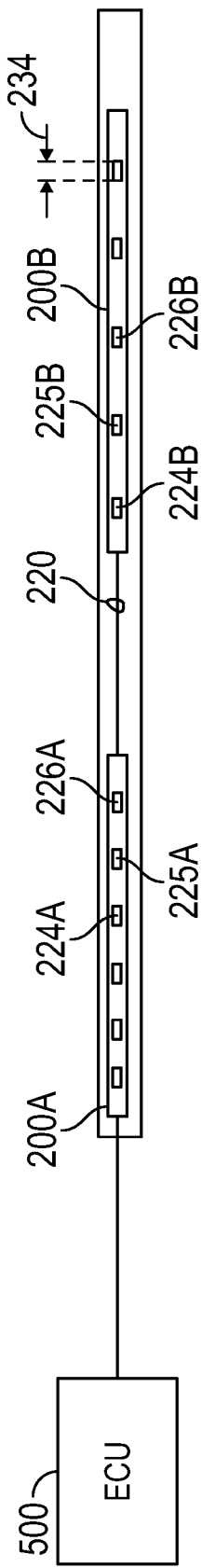
FIG. 14 is a perspective view of a seat belt webbing laid out flat showing first and second force sensors connected in a single circuit therein for communication with an associated electronic control unit as disclosed herein.
Figure 15:
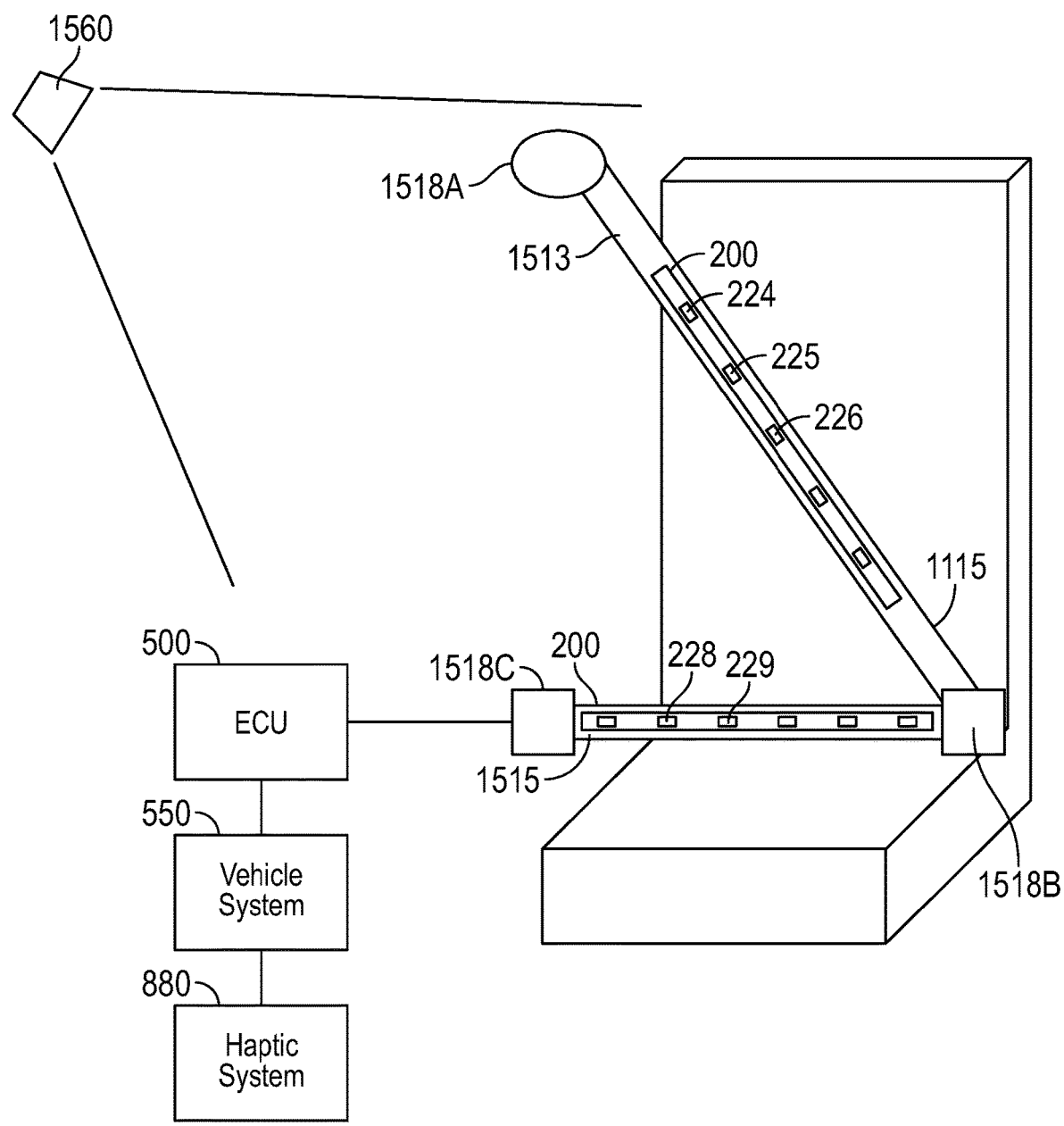
FIG. 15 is a perspective view of an occupant monitoring system having a field of view incorporating the seat belt sensor system of FIG. 10.

The seat belt embodiments of FIGS. 13-15 also illustrate numerous ways of using changes in capacitance to allow a seat belt to be a data transmission device with a flexible force sensor 200 as disclosed herein. FIG. 13 illustrates a concept of sliding one of the sensors into a respective pocket 1320 that can hold the sensor in proximity to an individual wearing the seat belt 1315 or for use with any other supporting structure proximate the seat belt. In this embodiment, the sensor may be portable and re-usable in other location with similar pocket structures to complete a modular assembly of sensors created in an ad hoc manner by the user.

FIG. 14 is another example illustrating that using the sensors 200 of this disclosure provides numerous opportunities to pair the appropriate sensors in a supporting structure to achieve a desired force measurement by detecting changes in capacitance. The example of FIG. 14 illustrates that multiple sensors 200A, 200B may have respective electrodes 224A, 225A, 226A and 224B, 225B, 226B that read capacitive changes individually but are connected in a data system connected to an electronic control unit 500, illustrated in FIG. 5. In this non-limiting embodiment, a seat belt 1415 may incorporate the flexible sensors 200A, 200B at respective positions on or within the seat belt 1415 by any of the attachment methods of this disclosure. Though the electrodes on each sensor operate individually to gather data regarding forces and pressures thereon, the overall assembly operates collectively to provide specialized data retrieved from each capacitive measurement area 234 for a global data processing function that allows a higher degree of resolution in force measurements at numerous supporting structures in the vehicle.

Figure 8:
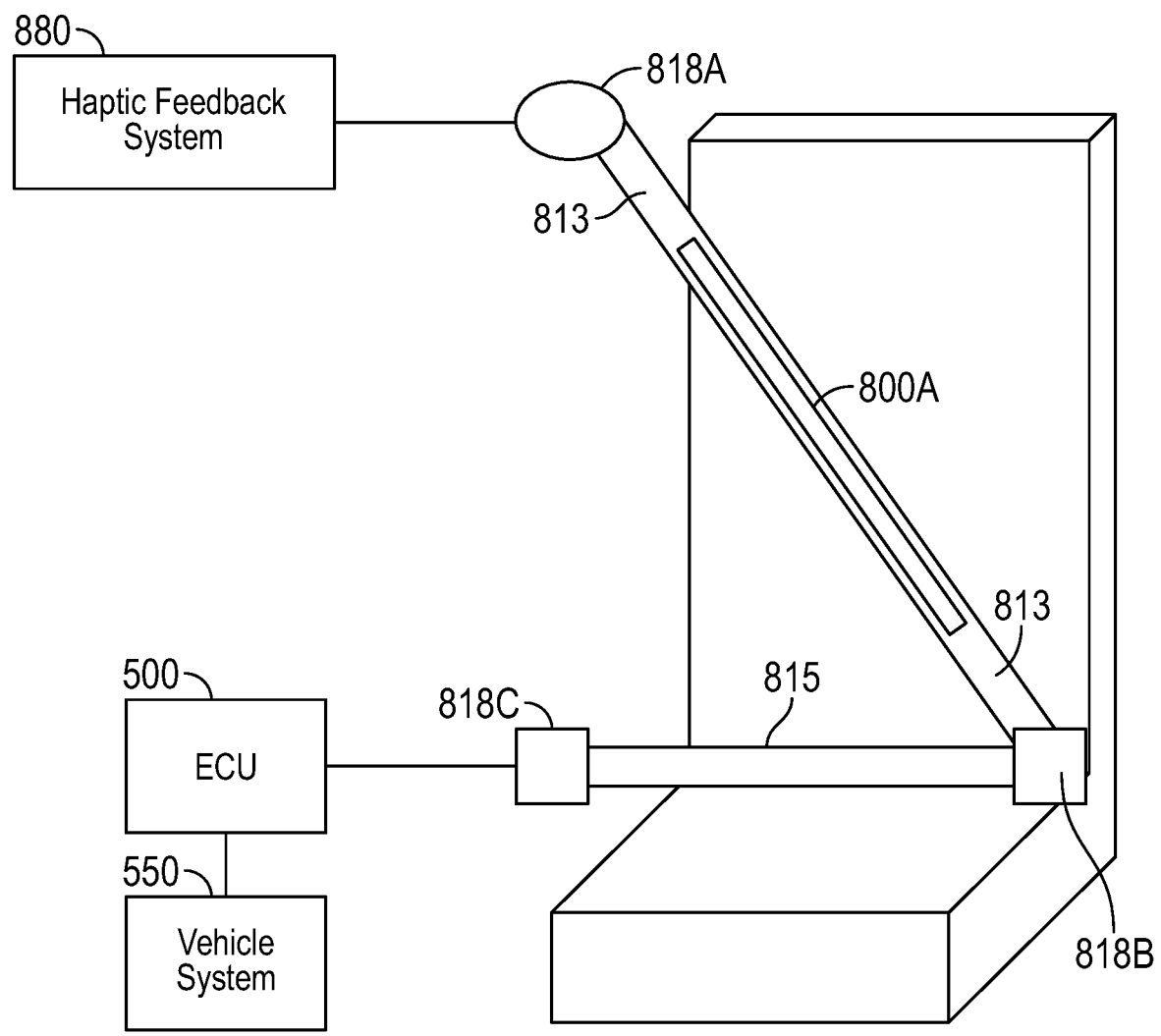
FIG. 8 is a front plan view of a vehicle seat belt configured with surface placement for at least one force sensor in communication with an electronic control unit connected to a control system for vehicle electronics, including a haptic actuator feature, according to this disclosure.
Figure 9:
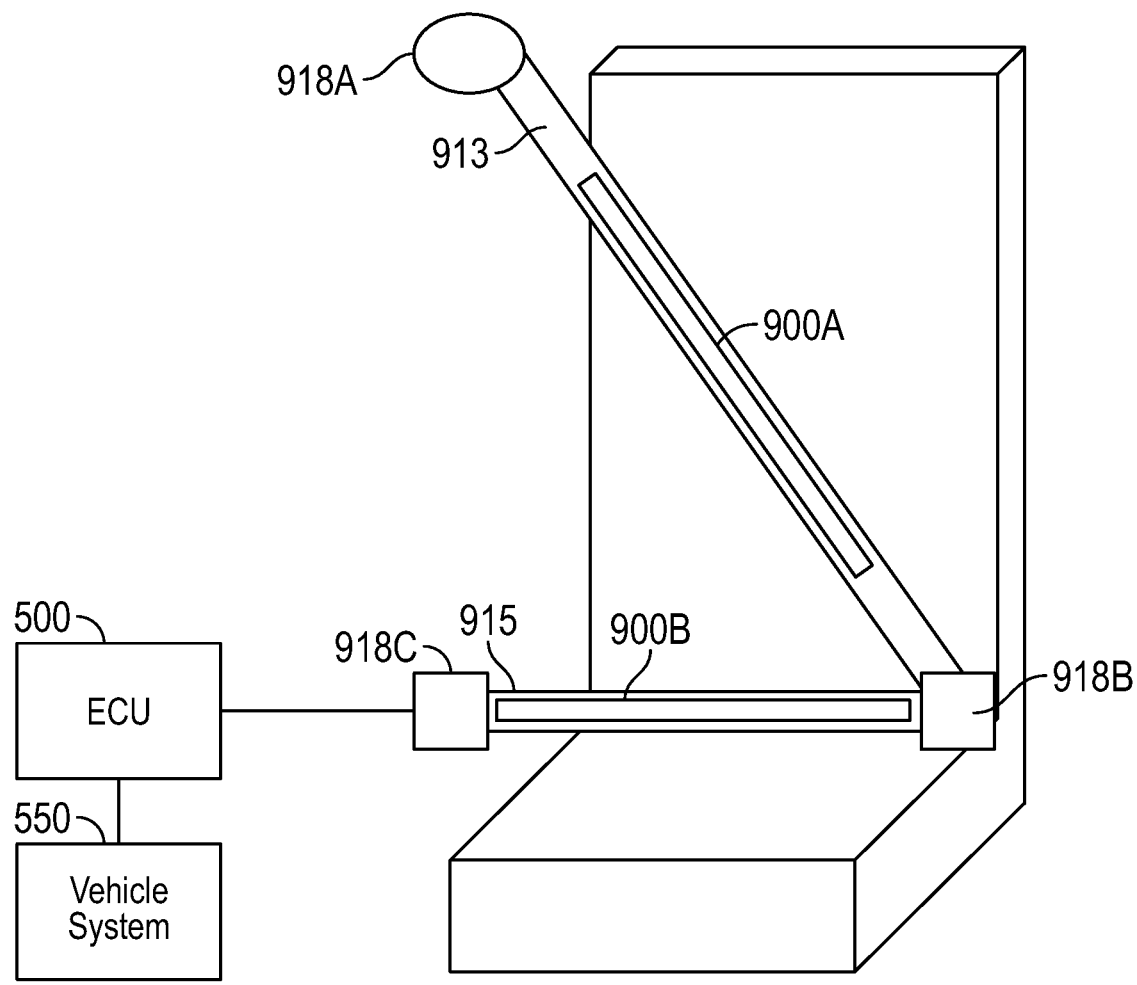
FIG. 9 is a front plan view of a vehicle seat belt configured with surface placement for at least one force sensor on a shoulder strap and an associated lap belt according to this disclosure.
Figure 10:
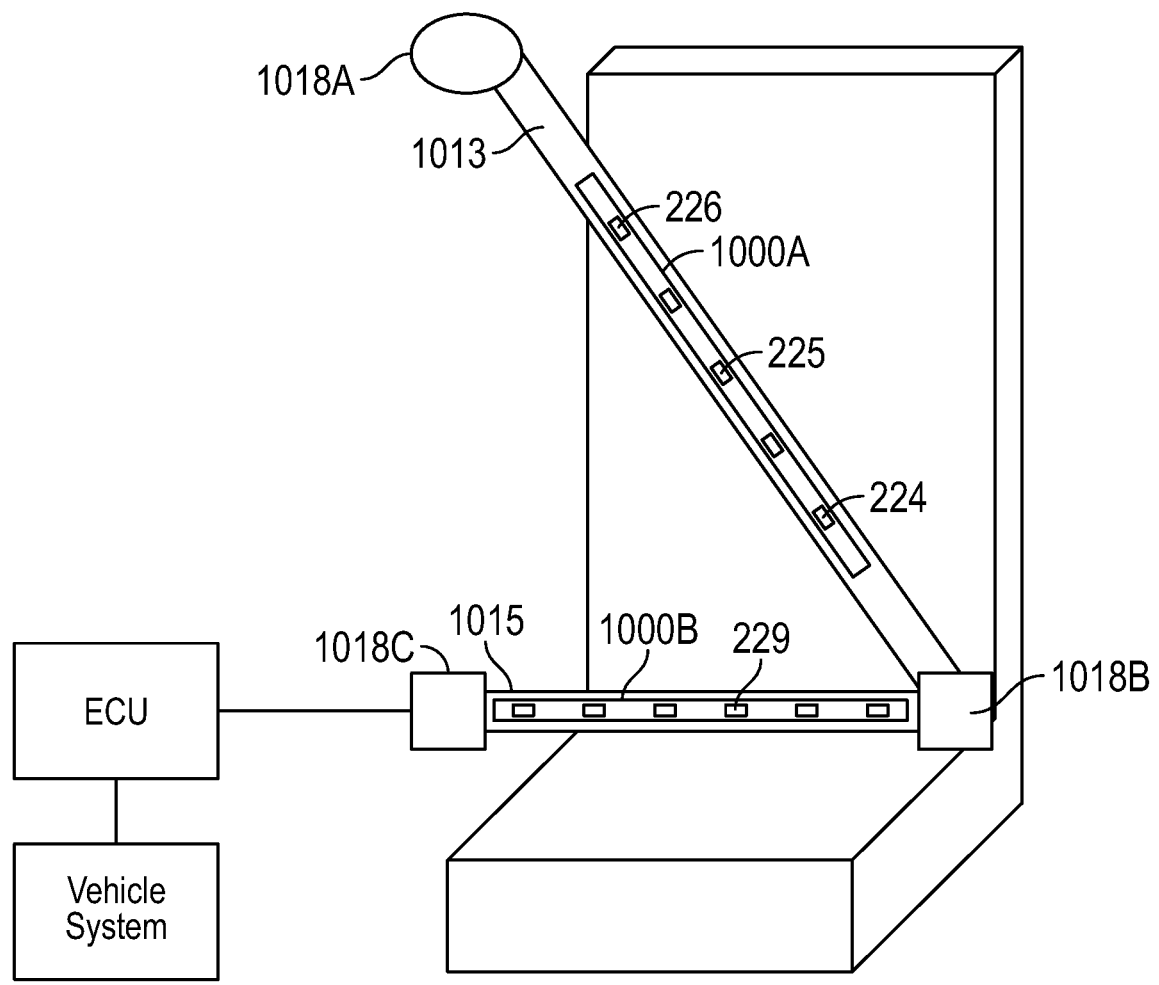
FIG. 10 is a front plan view of a vehicle seat belt configured with surface placement for a plurality of sensing nodes on at least one force sensor on a shoulder strap and an associated lap belt according to this disclosure and communications hardware to a network as discussed below.
Figure 11:
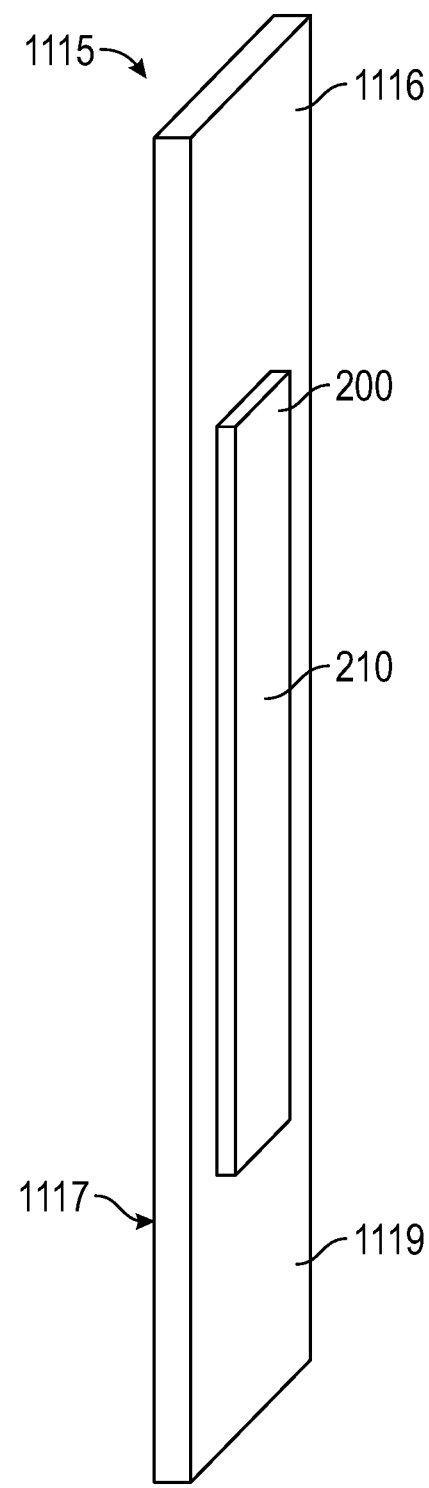
FIG. 11 is a perspective view of the force sensor laminated to an occupant side of a seat belt webbing according to the embodiments herein.

FIG. 15 is an example schematic of other embodiments that include a seat belt sensor assembly having a seat belt webbing 1513, 1515, a plurality of force sensors 200 coupled to the seat belt webbing, wherein the force sensor captures force levels applied to the force sensor. An electronic control unit 500, having a processor communicatively coupled with a memory storing computer-readable instructions, executes the computer-readable instructions stored on the memory. The computer-readable instructions cause the processor to receive the force levels from the force sensor and determine if a respective force level is greater than or equal to a minimum threshold force value and, if the respective force level is greater than or equal to the minimum threshold force value, control a vehicle system. The vehicle system may include any of the following systems: an infotainment system, a cruise control system, an autonomous driving control system, an occupant health system, and a motorized seat belt retractor system. The vehicle system may be an occupant health system and controlling the occupant health system may include receiving a series of force levels from the force sensor over a period of time, determining an occupant respiration condition based on changes in the series of force levels over the period of time, and sending an alert to an occupant if the occupant respiration condition indicates an emergency situation. In at least one embodiment, controlling the occupant health system further includes sending a control message to an autonomous driving control system, the control message causing the autonomous driving control system to safely bring the vehicle to a stop. Sending an alert to the occupant comprises any of the following: sending a visual warning to an infotainment system display, sending an audio warning to a vehicle sound system, and sending a haptic warning to a haptic feedback system. As illustrated in FIGS. 8 and 15, the seat belt sensor assembly may also include a haptic feedback system 880 coupled to the seat belt sensor assembly, wherein the computer-readable instructions further cause the processor to send a haptic feedback signal to the haptic feedback system, causing the haptic actuator to provide a haptic response to the occupant. In one non limiting embodiment, the haptic actuator may be positioned proximate to a seat belt retractor assembly 1518, such as within the above described D-rings associated with seat belt positioning in the vehicle. The haptic response to the occupant comprises a tactile or audio component. In one non-limiting embodiment, the haptic response may be a tactile messaging in which the seat belt 1115 tugs at the occupant with either or both portions of the shoulder strap webbing and the lap belt webbing. Examples of using haptic responses in various components of a vehicle and the associated structures are described in commonly owned U.S. Patent Pub. No. 20180194369, which is incorporated herein in its entirety.

A seat belt sensor system according to this disclosure is suitable for data transmission to controllers and computers that are also associated with other occupant monitoring systems. In one embodiment, the force sensor is attached to a seat belt webbing, and the force sensor captures a force level of a touch applied to the force sensor, wherein the force sensor includes discrete activation zones as described above. A vehicle utilizing this technology may also include an occupant monitoring system, wherein the occupant monitoring system has a camera with a field of view incorporating the discrete activation zones. An electronic control unit includes a processor communicatively coupled with a memory, the memory storing computer-readable instructions, wherein the processor executes the computer-readable instructions stored on the memory, the computer-readable instructions causing the processor to receive a series of images from the camera, analyze the series of images to determine a force sensor condition, selectively activate/deactivate the discrete activation zones based on the force sensor condition, receive the force level from the selectively activated zones and determine if the force level is greater than or equal to a minimum threshold force value. If the force level is greater than or equal to the minimum threshold force value, the system allows for control of another vehicle system.

As noted above the flexible force sensor of this disclosure may be installed in any number of support structures in the vehicle that benefit from compression, pressure, and tension measurements and/or touch sensing functions. One of these applications is that of a child safety seat installed in a vehicle.

Currently, Child Restraint Systems (CRS) are installed incorrectly by up to 85% of parents (NHTSA 2009). Currently, no methods in the vehicle are available for the car to let the user know if or when a child seat is installed incorrectly, and rely on the users' review of the vehicle user guide as well as the CRS manufacturers own documentation. CRS manufacturers documentation is generally more thoroughly read than the owners' manual, leading to these unsafe conditions. Providing parents with an indication of the potentially unsafe installation of these systems could drastically reduce the number of incorrect installations on the road.

Using a force sensing seat belt, determining the efficacy of the seat belt routed through the CRS could be modelled and reported on with a detailed study. Monitoring the pressure and position of the belt as it is mounted could be leveraged to provide the vehicle operator with an indication that the belt may not be routed correctly, or the tension is not sufficient to provide adequate protection in the event of a collision. This could also be expanded to provide optimal anchoring for belt mounted CRS. Detailing specifically where high pressure points occur in these specific use cases could be leveraged for better understanding of potential modes of failure of the belt system and could also provide the vehicle operator feedback if and when the CRS is installed improperly/unsafely.

Providing the vehicle operator with any additional feedback that could be leveraged to keep their child safe would be a large improvement to the current status for CRS that rely on belt routing, specifically boosters and for vehicle owners that opt to use the belt in lieu of the LATCH system present in vehicles for whatever reason.

Figure 18:
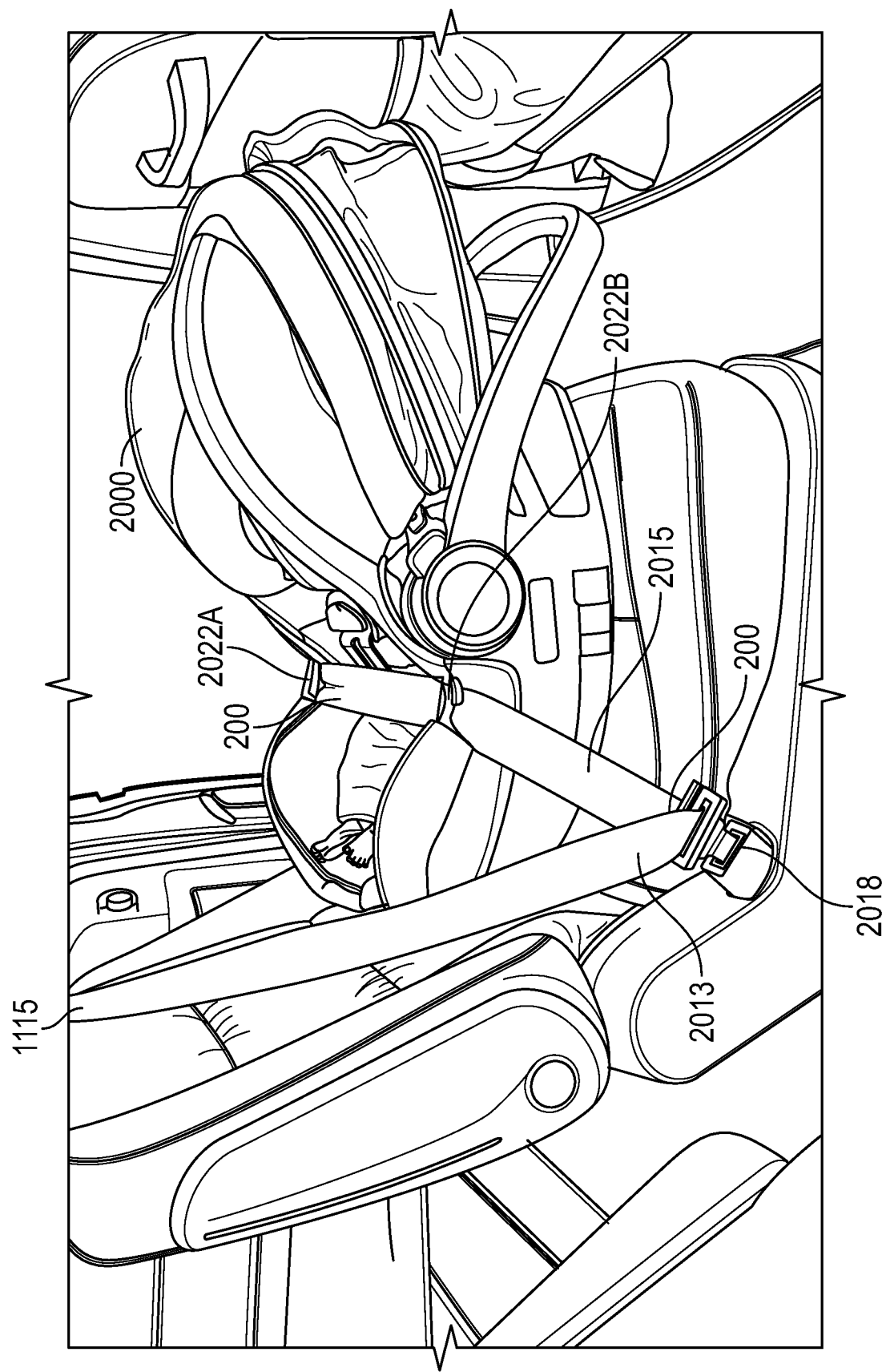
FIG. 18 is a side perspective view of a child restraint system held in place with a vehicle seat belt having force sensor installations in accordance with this disclosure.
Figure 19:
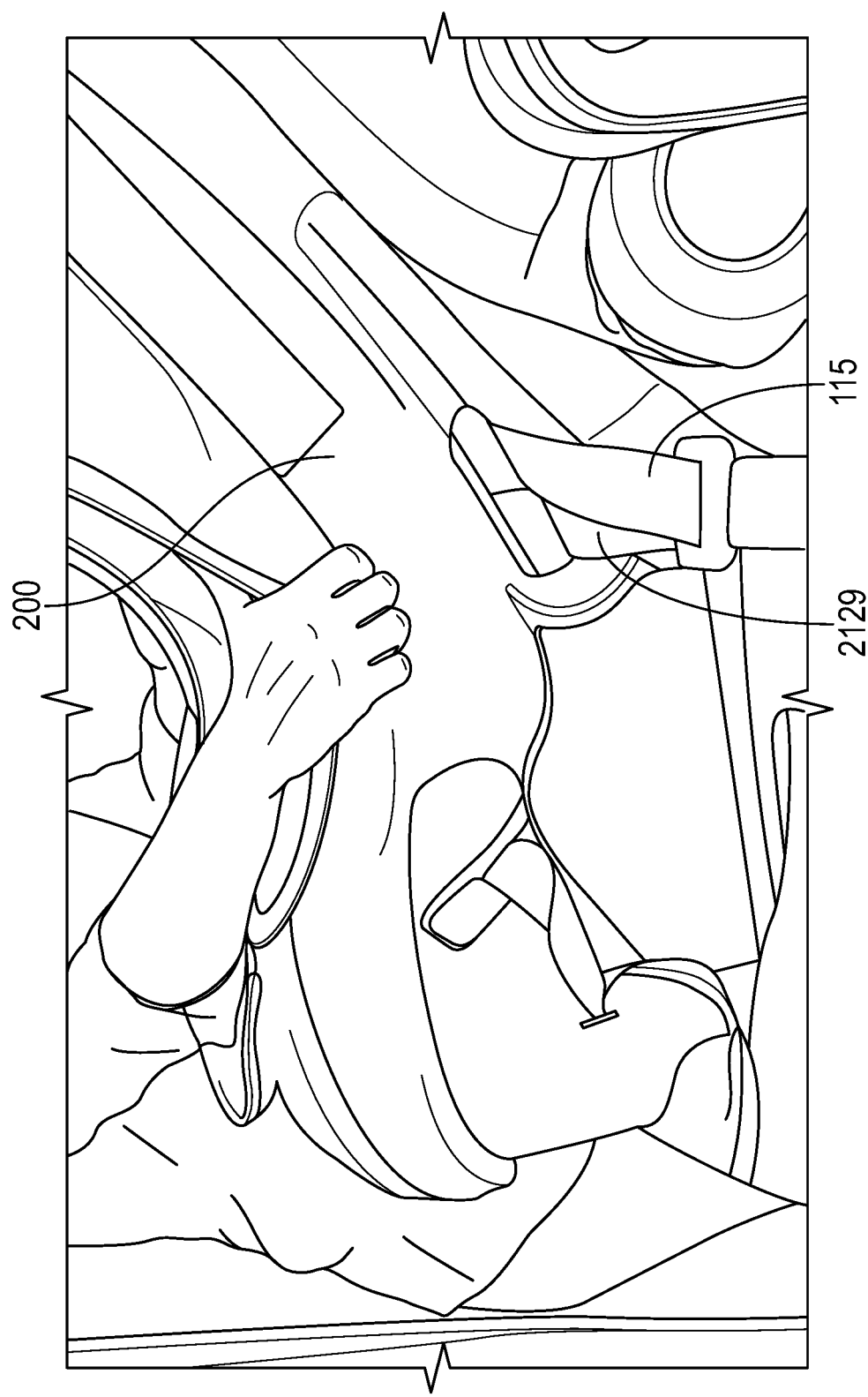
FIG. 19 is a side perspective view of a child restraint system held in place with a vehicle seat belt having force sensor installations in accordance with this disclosure.

In this regard, as shown herein, FIGS. 18-19 illustrate car seat straps and seat belt webbing assemblies 2013, 2015 that are compatible with the technology disclosed for a pressure sensing force sensor having capacitive sensors in communication with process control equipment. In these embodiments, compression of the deformable dielectric layer 230 may be used to indicate the pressure at which a seat belt webbing 2013, 2015, 2215 exerts forces onto a force sensor 200 sandwiched against regions of a child safety restraint system. Similar to the above described procedures for determining proper use of a seat belt by a vehicle occupant, the force sensor data may also be used to indicate appropriate tensions and pressure data showing proper securing of a child safety restraint, particularly at anchor points 2018 that are critical for proper and reliable car seat installation. In these embodiments, and without limiting this disclosure, the supporting structures of importance are portions of the car seat assemblies acting on the flexible sensors at critical points where the car seat and the seat belts, or other straps, intersect. The forces measured along the seat belt holding the child restraint system, the compression of the force sensors positioned in the seat belt, and the associated readings for pressure and tension can be used to electronically monitor child safety restraint system installations, including but not limited to car seats and booster seats.

Considering FIG. 18 as one non-limiting example, a child restraint system may include a rear facing infant car seat 2000 held in place with a vehicle seat belt 1115 having a shoulder strap webbing 2013 and a lap belt webbing 2015, adapted for use to hold the car seat 2000 securely in place according to all safety regulations. Force sensors 200 of this disclosure may be used at any points along the respective webbings 2013, 2015 at whatever orientation and attachment mechanism described herein is most effective. The supporting structures interacting with the force sensors in this example, may be a clasp at the seat belt buckle 2018 along with the sides or the top of the car seat, particularly at the arm openings 2022A, 2022B through which the seat belt 1115 tightens onto the car seat 2000. Force sensors 200 of this disclosure are flexible and bendable to proper radii to enable accurate detection of capacitance changes in any location, illustrating degrees of compression, magnitudes and directions of forces, as well as pressure and tension readings. The force sensors are designed for accuracy even at certain inflection points along the seat belt (i.e., at points where the seat belt turns directions at the buckle 2018 or at the arm openings 2022A, 2022B). The measurements collected by a computer in data communication with the force sensors 200 enable extremely accurate seat belt positioning for safely securing a child restraint system during vehicle operation.

FIG. 19 illustrates another kind of child restraint system for a toddler in which the seat belt 1115 holds a front facing car seat 2100 in place by threading the seat belt 1115 through bottom openings of the car seat. These attachment points may be in addition to mechanical anchor systems of newer vehicles meant to mate with corresponding hardware on the child car seat 2100. Similar to the discussion of FIG. 18, the force sensors described herein are equally adapted to measure forces along the length of the seat belt webbing 2129, particularly in areas that are not visible to the user. This embodiment provides an integrity check for supporting structures that are not easily discernible with the naked eye.

In another embodiment, the technology of this disclosure may be used to improve use of motorized seat belt assemblies. Current implementations of a motorized seat belt idealize the occupant as a standard 50th percentile adult male. The tension for a seat belt tailored to the stature of that individual may or may not be ideal for occupants that fall far outside that range (i.e. 5th percentile female, 95th percentile male) and needs to be optimized with force sensors embedded in or attached to a seat belt operated with a motorized seat belt assembly.

The embodiments herein may include using force sensors 200 of this disclosure in conjunction with motorized seat belt assemblies that are currently in development and optionally controlled with a motor control system. The motor control system will receive feedback from various occupant sensors in the cabin (i.e. force sensing seat belt, occupant monitoring system, driver monitoring system, seat sensors, etc.) to automatically adjust the tension on a seat belt 1115 to best accommodate the vehicle occupant. This can be done to provide the optimal belt pressure by increasing or decreasing seat belt factors that are adjustable, either automatically or manually, such as but not limited to the angle of the belt as it approaches the occupant's shoulder, the length of the seat belt extended, and the payout factors for a given user during emergency restraint operations. When combined with a force sensing seat belt, this can be done highly accurately to ensure even pressure across the chest.

Accordingly, force sensors of this disclosure may be connected to a vehicle system including a motorized seat belt retractor system for controlling the retractor system. For ease of reference, this disclosure incorporates by reference United States Patent Pub. No. 20200247353 explaining non-limiting examples of retractor systems that may benefit from the force sensors and uses thereof described in this disclosure. The method of controlling a motorized seat belt retractor system may include receiving a series of force levels from the force sensors 200 over a period of time, determining a seat belt slack condition based on changes in the series of force levels over the period of time; and sending a control message to the motorized seat belt retractor system, wherein the control message causes a motor to retract the seat belt webbing until a predetermined threshold force level is reached. The changes in total capacitance at numerous points along a seat belt webbing as shown in this embodiment correlate to not only seat belt height discussed above relative to an automated seat belt D-ring position adjuster, but also to retractors controlling seat belt extension in many applications including motorized seat belts. For numerous embodiments, this disclosure generally incudes an electronic controller that analyzes, via algorithms programmed in software, the pressure values sensed between portions of the seat belt and an occupant body, or some other supporting structure. This data may be transmitted as feedback to a motorized seat belt system and used to dynamically adjust seat belt tension in the vehicle. In some embodiments, an electronic controller uses the pressure values as feedback to a motorized seat belt system and dynamically adjusts seat belt tension in real time.

In one non-limiting embodiment, a motorized seat belt (MSB) includes an active restraint system that may have a seat belt retractor 2500 connected to an electric disc motor utilizing a rotor and a stator, the rotor being directly attached to the belt reel 2504, and a control unit connected to the disc motor is adapted to control the disc motor to drive the belt reel 2504 in accordance with a determined belt motion profile stored in an associated computer and computerized memory. In this example embodiment, this disclosure also includes motorized seat belt systems in which the belt reel 2504 is directly attached to a driveshaft of an electric motor to accomplish more advanced versions of motorized seat belts for modern smart vehicles.

Figure 20:
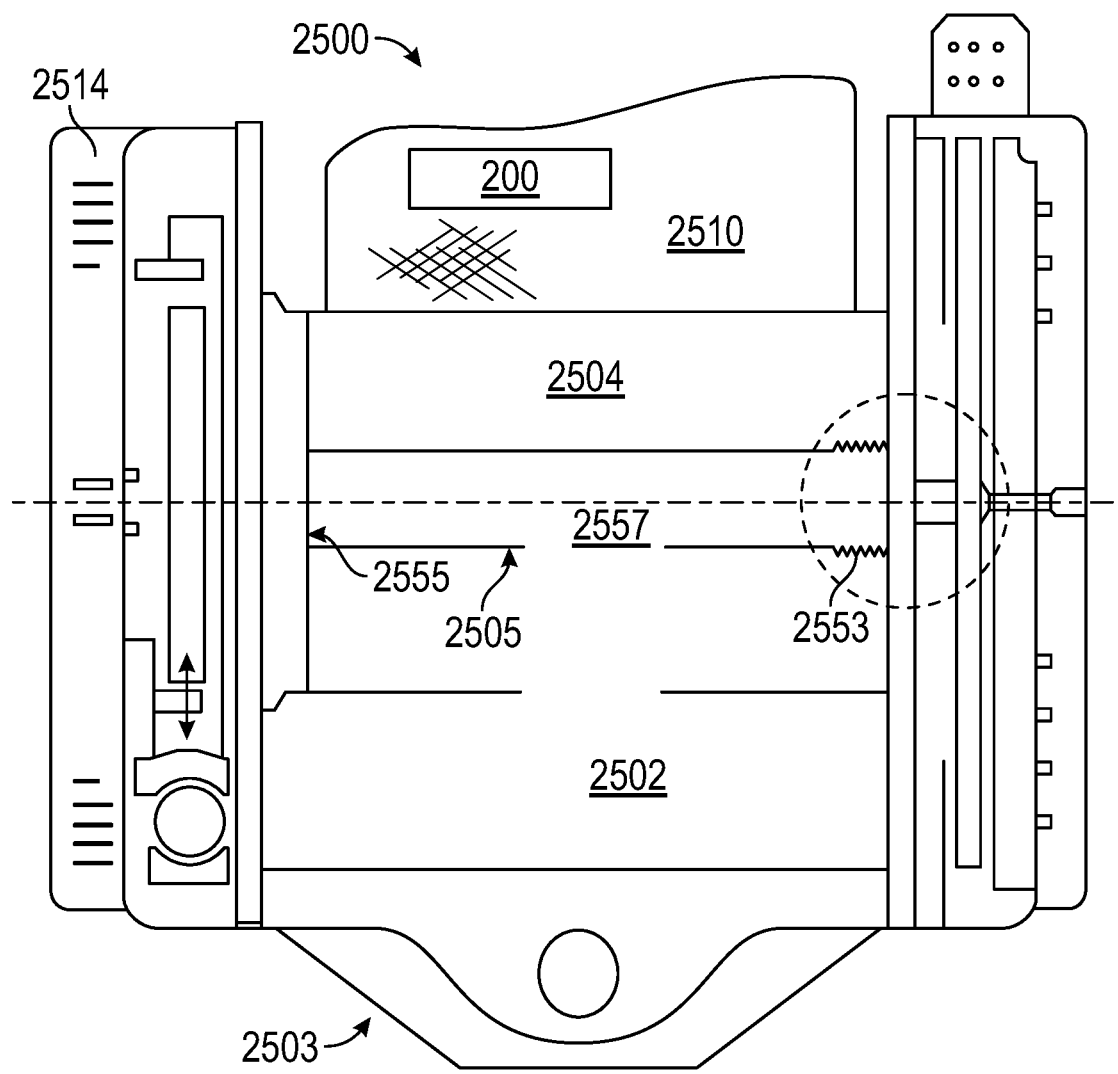
FIG. 20 is a front plan view of a seat belt retractor controlled with data gathered according to embodiments of this disclosure.

In an example embodiment shown schematically in FIG. 20, the seat belt retractor 2500 includes a frame 2503 and a belt reel 2504 with a belt webbing 2510 wound thereon which is rotatably supported by the frame for allowing winding and unwinding the belt webbing. Certain sensors within the restraint system are known and may include a belt reel position sensor of numerous kinds that help determine the length of the seat belt extended by a user. For example, one such sensor measures the thickness of the webbing wound onto the belt reel, whereas other kinds of sensors determine belt reel positions by measuring current at the disc motor. Based on the determined belt reel position it is known how much webbing is on the belt reel 2504 and how much webbing is taken off. Thus, the size of the passenger can be inferred, and out-of-position passengers, or the presence of a child seat can also be inferred. A torsion bar 2552 may be positioned within the belt reel 2504 as a load limiter. The torsion bar 2504 is attached via a fixed bearing to the belt reel on one side 2553 and unattached on the other side 2555, as shown, for example in FIG. 20.

The systems and methods of this disclosure account for proper payout during quick stops requiring emergency restraint operations with respect to a vehicle occupant. Using the above referenced torsion bar 2504 as a limit on payout load requires controls for different body types so that quick stops, restrained by a seat belt 1115, are safe and pre-programmed according to regulatory standards. By strategically placing force sensors 200 along the seat belt 1115, tension on the belt and effects at the torsion bar 2504 can be monitored throughout seat belt use.

As noted above, a computerized system of adjusting seat belt tension, seat belt length, seat belt position, and proper seat belt use may access adjustable and tunable energy absorption profiles for different use cases and different vehicle occupants. Such an algorithm can be adjusted to account for particular occupant parameters by communicating with and sharing data with an associated vehicle monitoring system, force sensors described herein, and overall vehicle control data gathered throughout the vehicle.

Integrating the force sensors of this disclosure with numerous other computerized safety systems described herein allows for an overall vehicle control system to monitor an entire experience for drivers and passengers. Each of the different kinds of sensor data, whether force sensor data, optical data, electrical data, and the like can play a role to piece together the entire picture of an occupant's safety profile. The force sensors described herein, therefore, are configured for integrating with other monitoring systems such as an occupant monitoring system to confirm activities sensed by a seat belt assembly, including but not limited to HMI inputs, sections of seat belts subject to specifically identified forces and the sources of those forces, as well as projected and actual physical manifestations of proper safety equipment use.

Although the present disclosure has been described in detail with reference to particular arrangements and configurations, these example configurations and arrangements may be changed significantly without departing from the scope of the present disclosure. For example, although the present disclosure has been described with reference to particular communication exchanges involving certain network access and protocols, network device may be applicable in other exchanges or routing protocols. Moreover, although network devices are illustrated with reference to particular elements and operations that facilitate the communication process, these elements, and operations may be replaced by any suitable architecture or process that achieves the intended functionality of network device.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. The structures shown in the accompanying figures are susceptible to 3-D modeling and can be described relative to vertical, longitudinal and lateral axes established with reference to neighboring components as necessary.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. Note also that an "application" as used herein this Specification, can be inclusive of an executable file comprising instructions that can be understood and processed on a computer, and may further include library modules loaded during execution, object files, system files, hardware logic, software logic, or any other executable modules.

In example implementations, at least some portions of the activities may be implemented in software provisioned on networking device. In some embodiments, one or more of these features may be implemented in computer hardware, provided external to these elements, or consolidated in any appropriate manner to achieve the intended functionality. The various network elements may include software (or reciprocating software) that can coordinate in order to achieve the operations as outlined herein. In still other embodiments, these elements may include any suitable algorithms, hardware, software, components, modules, interfaces, or objects that facilitate the operations thereof.

Furthermore, computer systems described and shown herein (and/or their associated structures) may also include suitable interfaces for receiving, transmitting, and/or otherwise communicating data or information in a network environment. Additionally, some of the processors and memory elements associated with the various nodes may be removed, or otherwise consolidated such that single processor and a single memory element are responsible for certain activities. In a general sense, the arrangements depicted in the Figures may be more logical in their representations, whereas a physical architecture may include various permutations, combinations, and/or hybrids of these elements. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc.

In some of example embodiments, one or more memory elements (e.g., memory can store data used for the operations described herein. This includes the memory being able to store instructions (e.g., software, logic, code, etc.) in non-transitory media, such that the instructions are executed to carry out the activities described in this Specification. A processor can execute any type of computer readable instructions associated with the data to achieve the operations detailed herein in this Specification. In one example, processors (e.g., processor) could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

These devices may further keep information in any suitable type of non-transitory storage medium (e.g., random access memory (RAM), read only memory (ROM), field programmable gate array (FPGA), erasable programmable read only memory (EPROM), electrically erasable programmable ROM (EEPROM), etc.), software, hardware, or in any other suitable component, device, element, or object where appropriate and based on particular needs. Any of the memory items discussed herein should be construed as being encompassed within the broad term 'memory element.' Similarly, any of the potential processing elements, modules, and machines described in this Specification should be construed as being encompassed within the broad term "processor."

These and other aspects of this disclosure are set forth in the claims below.

The invention claimed is:

1. A seat belt sensor assembly comprising:
a seat belt webbing;
a human machine interface on the seat belt webbing comprising a plurality of force sensors coupled to the seat belt webbing, wherein the force sensors comprise discrete activation zones having a perimeter defined by respective electrodes that capture force levels applied to the discrete activation zones and transmit the force levels as capacitive measurements to an electronic control unit, wherein the capacitive measurements comprise a direct relationship between the force levels and a sensed capacitance at respective discrete activation zones;
wherein the electronic control unit comprises a processor communicatively coupled with a memory, the memory storing computer-readable instructions that implement software with the processor; and
a map of force sensor locations on the seat belt webbing stored in the memory,
wherein the processor of the electronic control unit executes the software to:
receive from the discrete activation zones the capacitive measurements from the force sensors;
calculate capacitive response tracking data for each of the discrete activation zones according to the map of force sensor locations;
identify user commands from the capacitive response tracking data; and
control a vehicle system with the user commands.

2. The seat belt sensor assembly of claim 1, wherein the vehicle system comprises any of the following systems: an infotainment system, a cruise control system, an autonomous driving control system, an occupant health system, and a motorized seat belt retractor system.

3. The seat belt sensor assembly of claim 1, wherein the vehicle system comprises an occupant health system and controlling the occupant health system comprises:
receiving a series of capacitive measurements from the force sensors over a period of time;
determining an occupant respiration condition based on changes in the series of capacitive measurements over the period of time; and
sending an alert to an occupant if the occupant respiration condition indicates an emergency situation.

4. The seat belt sensor assembly of claim 3, wherein controlling the occupant health system further comprises:
sending a control message to an autonomous driving control system, the control message causing the autonomous driving control system to safely bring the vehicle to a stop.

5. The seat belt sensor assembly of claim 3, wherein sending an alert to the occupant comprises any of the following: sending a visual warning to an infotainment system display, sending an audio warning to a vehicle sound system, and sending a haptic warning to a haptic feedback system.

6. The seat belt sensor assembly of claim 1, further comprising a haptic feedback actuator coupled to the seat belt sensor assembly, wherein the software further causes the processor to send a haptic feedback signal to the haptic feedback actuator, causing the haptic actuator to provide a haptic response to the occupant.

7. The seat belt sensor assembly of claim 6, wherein the haptic response to the occupant comprises a tactile or audio component.

8. The seat belt sensor assembly of claim 1, wherein the force sensor comprises a stretchable and flexible sensor array with discrete activation zones.

9. The seat belt sensor assembly of claim 1, wherein at least one of the force sensors is coupled to an occupant side of the seat belt webbing.

10. The seat belt sensor assembly of claim 1, wherein at least one of the force sensors is laminated to an occupant side of the seat belt webbing.

11. The seat belt sensor assembly of claim 1, wherein at least one of the force sensors is laminated between layers of the seat belt webbing.

12. The seat belt sensor assembly of claim 1, wherein at least one of the force sensors is positioned in a seat belt webbing pocket.

13. The seat belt sensor assembly of claim 1, wherein at least one of the force sensors is comprised of at least two force sensors connected in a single circuit.

14. The seat belt sensor assembly of claim 1, wherein the seat belt webbing comprises a chest portion and a lap portion.

15. The seat belt sensor assembly of claim 14, wherein a first force sensor is coupled to an occupant side of the seat belt webbing chest portion and a second force sensor is coupled to an occupant side of the seat belt webbing lap portion.

16. The seat belt sensor assembly of claim 1, wherein the vehicle system comprises a motorized seat belt retractor system and controlling the motorized seat belt retractor system comprises:
receiving a series of capacitive measurements from at least one of the force sensors over a period of time;
determining a seat belt slack condition based on changes in the series of capacitive measurements over the period of time; and
sending a control message to the motorized seat belt retractor system, wherein the control message causes a motor to retract the seat belt webbing until a predetermined threshold force level is reached.

17. The seat belt sensor assembly of claim 1, wherein the force levels applied to the force sensors comprise a touch by any of the following manual manipulations: a discrete press and release, a pinch, a pinch and slide, and a gesture.

18. A seat belt sensor system in a vehicle, comprising:
a seat belt webbing inside the vehicle;
an occupant monitoring system, wherein the occupant monitoring system comprises a camera in the vehicle with a field of view incorporating portions of the seat belt webbing;
a plurality of force sensors coupled to the seat belt webbing and defining discrete activation zones corresponding to respective electrodes on the seat belt webbing, wherein the force sensors capture a force level applied onto both sides of the seat belt webbing to respective discrete activation zones and wherein the respective electrodes transmit the force levels as capacitive measurements to an electronic control unit,
wherein the electronic control unit comprises a processor communicatively coupled with a memory, the memory storing computer-readable instructions and a map of the discrete activation zones on the seat belt webbing, wherein the processor executes the computer-readable instructions stored on the memory, the computer-readable instructions causing the processor to:
receive a series of images from the camera;
analyze the series of images to determine a force sensor condition;
selectively activate/deactivate the discrete activation zones based on the force sensor condition;
receive the capacitive measurements from selectively activated zones;
calculate capacitive response tracking data according to the map of the discrete activation zones;
identify user commands from the capacitive response tracking data; and
control a vehicle system with the user commands.

19. A seat belt sensor assembly comprising:
a seat belt webbing;
a human machine interface on the seat belt webbing comprising a plurality of force sensors coupled to the seat belt webbing, wherein the force sensors capture force levels applied to a surface and a different side of the force sensors and transmit the force levels as capacitive measurements to an electronic control unit,
wherein the electronic control unit comprises a processor communicatively coupled with a memory, the memory storing computer-readable instructions that implement software with the processor; and
a map of force sensor locations on the seat belt webbing stored in the memory,
wherein the processor of the electronic control unit executes the software to:
receive the capacitive measurements from the force sensors;
calculate capacitive response tracking data according to the map of force sensor locations;
identify user commands from the capacitive response tracking data; and
control a vehicle system with the user commands.

20. The seat belt sensor of claim 19 wherein each of the force sensors comprises an electrode that defines a discrete activation zone that transmits respective force levels as capacitive measurements to the electronic control unit.

* * * * *